(12) United States Patent
Lewis et al.

(10) Patent No.: US 12,350,510 B2
(45) Date of Patent: Jul. 8, 2025

(54) MAGNETIC MICROWIRES FOR ENERGY-TRANSPORTING BIOMEDICAL APPLICATIONS

(71) Applicant: Northeastern University, Boston, MA (US)

(72) Inventors: Laura Lewis, Boston, MA (US); Rafael Pèrez Del Real, Madrid (ES); Manuel Vázquez Villalabeitia, Madrid (ES); Abigail N. Koppes, Charlestown, MA (US)

(73) Assignee: Northeastern University, Boston, MA (US)

(*) Notice: Subject to any disclaimer, the term of this patent is extended or adjusted under 35 U.S.C. 154(b) by 435 days.

(21) Appl. No.: 17/066,418

(22) Filed: Oct. 8, 2020

(65) Prior Publication Data

US 2021/0101016 A1     Apr. 8, 2021

Related U.S. Application Data

(60) Provisional application No. 62/912,278, filed on Oct. 8, 2019.

(51) Int. Cl.
*A61N 2/00* (2006.01)
*A61K 9/00* (2006.01)

(52) U.S. Cl.
CPC ............ *A61N 2/006* (2013.01); *A61K 9/0009* (2013.01); *A61N 2/002* (2013.01)

(58) Field of Classification Search
CPC ....... A61N 2/006; A61N 2/002; A61K 9/0009
See application file for complete search history.

(56) References Cited

U.S. PATENT DOCUMENTS

| | | | | |
|---|---|---|---|---|
| 10,335,590 | B2 * | 7/2019 | Katnani | ............ A61N 1/0534 |
| 2003/0085809 | A1 * | 5/2003 | Antonenco | ........ G08B 13/2408 340/572.6 |
| 2008/0058893 | A1 * | 3/2008 | Naujokat | ........... A61N 1/36067 607/45 |

FOREIGN PATENT DOCUMENTS

| | | | | |
|---|---|---|---|---|
| AU | 2013201221 A1 * | 3/2013 | ............... | A61B 5/04 |
| WO | WO-2019152415 A2 * | 8/2019 | | |

OTHER PUBLICATIONS

Kozejova et al., J. Magnetism and Magnetic Materials 470 (2019) 2-5. (Year: 2017).*
Ajam et al., Sensor Netw Data Commun 2016, 5:1. (Year: 2016).*
Hudak et al., "Influence of fixation on magnetic properties of glass-coated magnetic microwires for biomedical applications." IEEE Transactions on Magnetics 51, No. 1 (2015): 1-4.
Hudak et al., "Addition of molybdenum into amorphous glass-coated microwires usable as temperature sensors in biomedical applications." physica status solidi (a) 213, No. 2 (Nov. 23, 2015): 377-383.
Baranov, S. A, "Cast Amorphous Magnetic Microwires for Medical Applications", Advances in Biotechnology and Microbiology, Vo. 8 (3) Feb. 2018, pp. 50-53.
Hergt et al., "Magnetic particle hyperthermia: nanoparticle magnetism and materials development for cancer therapy.", Journal of Physics: Condensed Matter, 18(38), S2919, (2006) 16 pages.
Zhukov et al., "Nanocrystalline and Amorphous Magnetic Microwires", Encyclopedia of Nanoscience and Nanotechnology, vol. 6, ed. H.S. Nalwa, Valencia, CA: American Scientific Publishers, 2004, p. 365-387.
University of Alabama at Birmingham, 2019, National Spinal Cord Injury Statistical Center, Facts and Figures at a Glance. Birmingham, AL; Rereieved from nscisc.uab.edu/Public/Facts%20and%20Figures%202020, 2 pages.
Ray et al., "Management of nerve gaps: Autografts, allografts, nerve transfers, and end-to-side neurorrhaphy", Exp Neurol. May 2010 ; 223(1): 25 pages. doi: 10.1016/j.expneurol.2009.03.031.
Schmidt et al., "Neural Tissue Engineering: Strategies for Repair and Regeneration.", Annual Review of Biomedical Engineering, 5(1), 293-347, 2003.
Park et al., "Optogenetic control of nerve growth", Scientific Reports, 5, Article No. 9669 (2015) p. 1-9.

* cited by examiner

*Primary Examiner* — Robert S Cabral
(74) *Attorney, Agent, or Firm* — Verrill Dana, LLP

(57) ABSTRACT

Methods and devices including amorphous magnetic microwires are provided for biomedical energy transfer for diagnosis or therapy, to promote cellular growth, or to deliver pharmaceutical agents. Applications of the technology include in sensors, actuators, and therapeutic coatings, and for increasing the amount, directionality, or length of nerve growth. The technology also can be utilized for nerve regeneration, hyperthermic treatment of tumors, vascular theranostics, probing a nerve, stimulating a nerve, sensing a biological condition, catheterization, and micro-actuation.

18 Claims, 17 Drawing Sheets

Illustrated cross-section of apparatus

MAGNETIC MICROWIRES FOR ENERGY-TRANSPORTING BIOMEDICAL APPLICATIONS

CROSS-REFERENCE TO RELATED APPLICATIONS

This application claims priority to U.S. Provisional Application No. 62/912,278, filed 8 Oct. 2019, the entirety of which is incorporated herein by reference.

BACKGROUND

Amorphous magnetic microwires are a form of highly responsive magnetic material with strongly directional physical properties and unique magnetoelastic interactions. Their geometry, ease of production, and their inexpensive constituents make them useful for a variety of applications (Vazquez, 2015). Magnetic microwires have been contemplated for use in article surveillance, including smart labels and tags, and for detection systems. Further uses include devices for identification, authentication, and shoplifting prevention. Magnetic microwires have found limited use in biomedical sensors (Chiriac, H, et al., 2007; Radovan, H, et al., 2015; Hernando, A, et al., 1988; Hudak, R, et al., 2016) and as radiation therapy dose concentrators (Baranov, S A, 2018).

While magnetic nanoparticles have been studied for treatment of disease and injuries, magnetic microwires have not been similarly applied (Hergt, R, et al., 2006; Zhukov, A, et al. 2004). Magnetic nanoparticles, and other nanoparticles, are difficult to control and contain when administered to a subject. It is not possible to remove magnetic nanoparticles from the body once they are introduced. Nanoparticles might be excreted through biological channels or they can accumulate in the renal system, with unknown consequences. When applied to injuries, nanoparticles are not able to bridge the gap of significantly large cuts and lacerations (Vijayavenkataraman, S, 2020). Devastating peripheral and central nervous system injuries often require healing of significant gaps between injured nerves. According to the National Spinal Cord Injury Statistical Center, 17,730 new cases of spinal cord injury (SCI) occur every year in the United States (University of Alabama at Birmingham, 2019). Of these, less than one percent will experience complete neurological recovery before being released from the hospital. This leads to a lifetime of struggle, as patients see an increase in unemployment, rehospitalization, healthcare costs, indicating the burden that this kind of injury places on the caretakers as well (Ray, W Z; Mackinnon, S E, 2010). Improved treatments of such injuries are needed.

SUMMARY

The present technology provides devices and methods including amorphous magnetic microwires for transfer of biomedical energy. The devices and methods can be utilized, for example, for enhancement of nerve growth using the amorphous magnetic microwires. The devices and methods may also be utilized for treatment or diagnosis of various other conditions, for example, cancer, vascular theranostics, infections, and delivery of therapeutics. The present technology provides amorphous magnetic microwires that can have distinct advantages over nanoparticles, for example, control of therapy and ease of removal thereafter. In some examples, the present technology can be utilized as a biomedical sensor, for biomedical energy transfer to enhance patient outcome, or as an actuator.

The present technology can be further summarized by the following features:

1. An implantable medical device comprising one or more magnetic microwires, the microwires comprising a magnetic material comprising an amorphous phase of a metal, metal alloy, or a combination thereof.
2. The medical device of feature 1, wherein the magnetic microwires comprise an alloy having a formula of $M_xMT_y$, wherein M is a metalloid, MT is a transition metal, x is an integer from 0 to 35, y is an integer from 1 to 85, and $(x+y) \leq 100$.
3. The medical device of feature 1 or feature 2, wherein the metal alloy is selected from the group consisting of CoFeSiB, CoMnSiB, CoFeSiBCrNi, and alloys containing Fe, B, and Si.
4. The medical device of any of the preceding features, wherein the magnetic material has a coercivity in the range from about −50 to 200 A/m (about 0.6 to about 2.5 Oe).
5. The medical device of any of the preceding features, wherein one or more of said magnetic microwires comprises a sheath of non-metallic material covering the magnetic material, wherein the non-metallic material comprises a glass or polymer material.
6. The medical device of feature 5, wherein the glass comprises borosilicate, silica glass, an oxide, or a combination thereof.
7. The medical device of feature 5, wherein the polymer material is selected from the group consisting of laminin, collagen, poly(vinyl alcohol), poly-(D or L)-lactide, polyurethane acrylate, polycaprolactone, and poly(3,4-ethylenedioxythiophene) polystyrene sulfonate.
8. The medical device of any of features 5-7, wherein the sheath comprises a releasable pharmaceutical agent or diagnostic agent.
9. The medical device of feature 8, wherein the pharmaceutical or diagnostic agent is selected from the group consisting of imaging agents, growth factors, cytokines, antibodies, aptamers, nucleic acids, and antitumor agents.
10. The medical device of any of the preceding features, wherein the device is selected from the group consisting of a neural probe, a nerve growth stimulator, a biosensor, a catheter, a tissue heater, and a micro-actuator.
11. The medical device of any of the preceding features, wherein the one or more microwires produce a magnetic field having a magnitude of about 150 Gauss to about 15000 Gauss.
12. The medical device of any of the preceding features, comprising a plurality of magnetic microwires arranged in parallel or according to a geometric pattern.
13. A method for stimulating the growth of an injured nerve in a subject, the method comprising:
   (a) providing the medical device of feature 12;
   (b) implanting the plurality of magnetic microwires in the subject at or near the injured nerve;
   (c) optionally inducing or increasing a magnitude of a magnetic field or inducing an electric current in the plurality of microwires using a field applied from outside the subject's body;
   whereby growth of the injured nerve is stimulated.
14. The method of feature 13, wherein the microwires produce a magnetic field having a magnitude of about 100 Gauss to about 15000 Gauss.
15. The method of feature 13 or feature 14, wherein the injured nerve is severed and comprises a gap between severed ends, and wherein the plurality of magnetic microwires forms a parallel bundle that bridges the gap.

16. The method of any of features 13-15, wherein the stimulated nerve growth is an increase in neurite number, density, directionality, length, or a combination thereof.

17. The method of any of features 13-16, further comprising contacting the injured nerve with a growth enhancer.

18. A method of transferring energy or information in a subject, the method comprising:
   (a) implanting the magnetic microwires of the device of any of features 1-12 in the subject's body, the microwires traversing from a first location within the subject's body to a second location within the subject's body;
   (b) transferring energy or information to the one or more magnetic microwires at the first location; and
   (c) receiving energy or information from the one or more microwires at the second location.

19. The method of feature 18, wherein energy is transferred and received, and the received energy is used to release a pharmaceutical or diagnostic agent, to provide hyperthermic treatment of a tumor, to stimulate a nerve or growth of a nerve, to sense a biological condition, to actuate another medical device, to charge a battery of another medical device, or a combination thereof.

20. The method of feature 18 or feature 19, further comprising:
   (d) removing the magnetic microwires from the subject's body.

As used herein, a neurite refers to a projection from the cell body of a neuron, for example, an axon or a dendrite. As neurons grow and develop, the projection of a neurite may be difficult to distinguish as an axon or a dendrite. There are receptors on developing neurites that can detect both positive and negative growth cues from directions in the surrounding space. The growth cues can be, for example, biomedical energy cues, physical growth cues, chemical growth cues or chemotropic gradients, magnetic, light, and electrical growth cues. A growth cue can be inhibitory or can stimulate neurite growth. As used herein, the term "nerve" can refer to an axon or dendrite extending from a single nerve cell or from more than one nerve cell, for example as a bundle. The term "nerve" may include glial cells, for example, Schwann cells.

As used herein, a microwire has an average diameter in the range between about 1 micron and about 1000 microns. The length of microwires can be from about 1 mm to several meters, as required without limit. As used herein, the term "average diameter" refers to the mean diameter of a wire determined from at least two positions along the length of the wire. An average diameter of more than one microwire can be calculated by averaging the average diameter of each microwire. The average diameter can be calculated with or without including the thickness of a coating. The microwires described herein can have a cross-sectional profile that is essentially round, a square, rectangular, trapezoidal shape, star-shaped, trigonal, or flat. The average distance between two or more microwires is calculated by measuring two or more distances between two or more microwires and averaging the two or more measurements.

As used herein, the term "biomedical energy" can be, for example, electrical energy, thermal energy, magnetic energy, or chemical energy. The transfer of biomedical energy refers to the transfer of biomedical energy from one location to another and can include the conversion of one form of energy to another (e.g., chemical to thermal energy or magnetic to electrical energy).

As used herein, transition metals include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, copernicium, actinium, ununnilium, unununium, and ununbium. As used herein, metalloids include boron, carbon, aluminum, silicon, germanium, arsenic, antimony, tellurium, polonium, selenium, and astatine. Examples of rare earth elements are cerium, dysprosium, erbium, europium, gadolinium, holmium, lanthanum, lutetium, neodymium, praseodymium, promethium, samarium, scandium, terbium, thulium, ytterbium, and yttrium.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

BRIEF DESCRIPTION OF THE DRAWINGS

Staining is for beta-III tubulin. The scale bar is 250 microns.

DETAILED DESCRIPTION

Figure 1:
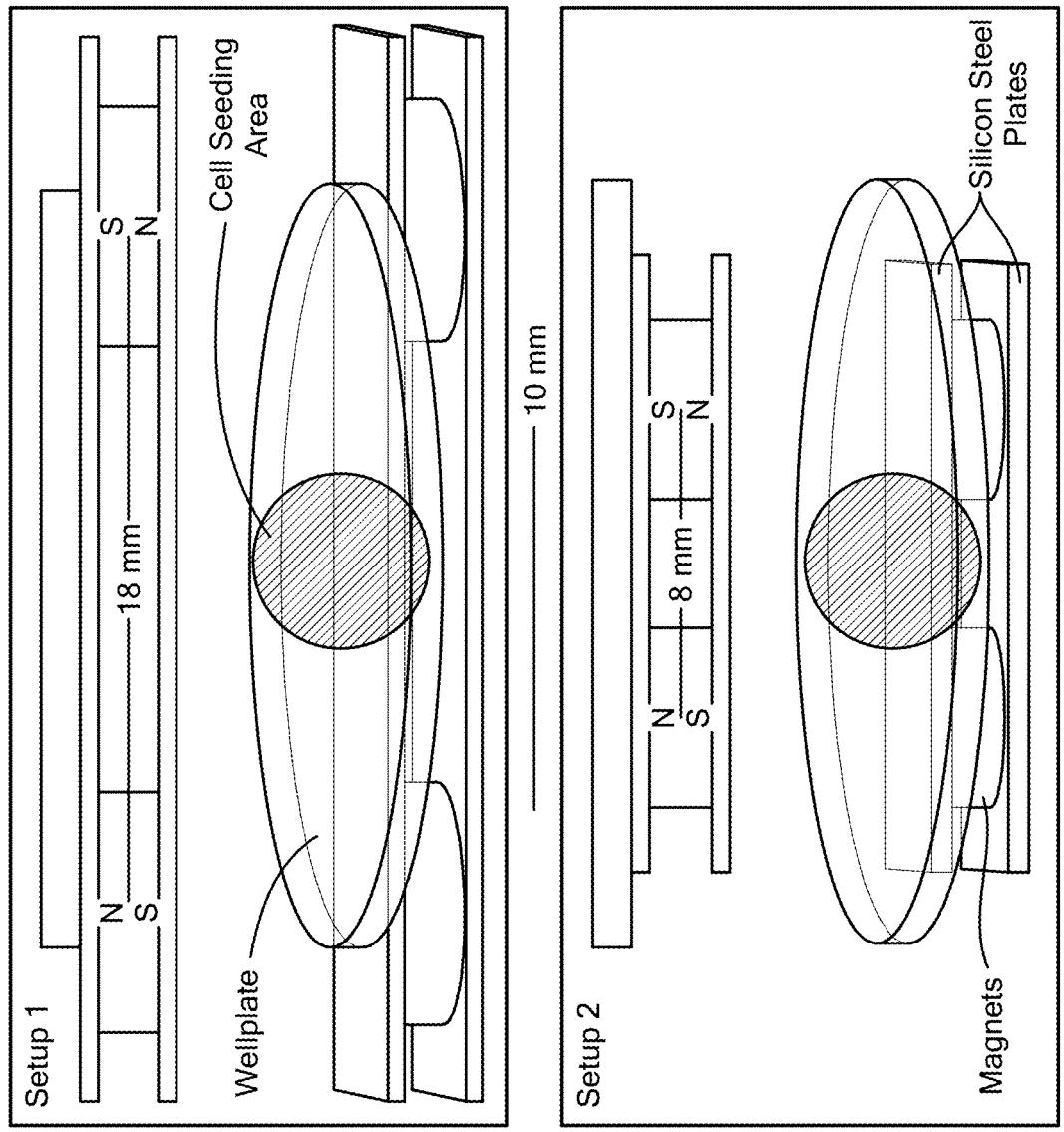
FIG. 1 shows an illustration comparing magnetic setup 1 (top, "Setup 1") for neurite growth and magnetic setup 2 (bottom, "Setup 2") for neurite growth. A 10 mm scale bar is shown at center.

The present technology provides the use of magnetic microwires to transfer energy or information from one location to another in a living organism for use in diagnostic or therapeutic applications, or to promote growth of neurons or other cells and tissues for wound healing. The applications of the technology provide more than existing sensing applications which involve only one-way information transfer. The magnetic microwires of the present technology have micron-scale diameter (e.g., in the range from about 1 to 1000 microns), can be passivated (non-reactive) surface, and include biocompatible constituents (such as Fe, Si, B). The magnetic microwires can be used for minimally invasive biomedical applications, for example, localized tumor hyperthermia, vascular theranostics, neural probes, and nerve stimulators. The nerve stimulators and methods can provide longer neurite outgrowth from growing neurons than other technologies, and can be utilized to steer or to change growth direction of a growing neuron while extending the growth, for example, to heal a severed nerve across a gap, such as from an injury.

The magnetic microwires in the present technology have numerous biomedical applications and offer control of treatments beyond that provided by nanoparticles containing similar materials. Some features of magnetic microwires of the present technology are: (i) flexibility, (ii) recoverability (i.e., can be easily removed from the body), (iii) small size (e.g., can be less than 100 micron diameter), (iv) biocompatibility (possessing an oxide or borosilicate coating), (v) controllable coercivity and, hence, heat dissipation under $H_{ac}$, (vi) high synthetic yield (km of length can be produced in one run), (vii) highly uniform properties, (viii) optionally coated with glass to allow light transmission, and (ix) tailorable composition adaptable for desired response.

Magnetically conductive amorphous microwires (i.e., microwires comprising or consisting of an amorphous magnetic material) can be made by a combination of elongation and rapid solidification of a melted, softened metal or alloy. The metal or alloy can be melted or liquefied and then rapidly cooled back to a solid phase. The rapid cooling can prevent the constituent atoms from returning to low-energy crystalline structure when the rate of crystal growth is less than the rate of heat loss. By controlling the linear velocity of a spinning wheel and the feed rate of the molten material, microwires of uniform diameter and shape can be produced. For low-cost production, the rapid cooling can be accomplished with a water quench. Rotating water-quenching can produce microwires with average diameters in the range from about 80-100 microns that possess a passivated oxide coating. Other liquids can be utilized for quenching, for example, oils, silicone liquids, and cryogenics. The Taylor-Ulitovsky method can utilize a drawing and quenching technique to yield glass-coated microwires with typical wire core diameters of 1-30 microns embedded in glass coatings of 2-5 microns in thickness. Other coatings can be utilized, and the difference between the coefficient of expansion between the alloy and the coating can be utilized to provide strain between the coating and alloy. Both of these examples of producing microwires can be used for a biomedical device application of the present technology. The magnetic character of these microwires may be tuned by low-temperature annealing that alters the short-range-order of the atomic configuration of the constituent elements. In this manner the magnetic response under applied AC magnetic field (applied from outside the body and requiring no physical connection to the embedded magnetic microwires other than through the magnetic field) can be tailored to defined parameters, including production of heat for hyperthermia applications.

The alloy that is generated from this process can be thermodynamically metastable, with compositions of the MxMTy form, where MT is one or more transition metal and M is one or more metalloid. Amorphous phase can be enhanced by combining different transition metals as MT and different metalloids as M, and other metals and additives can be utilized in the alloy. Examples of alloys include iron, silicon, and boron, creating an iron-borosilicate metallic glass alloy. Phase diagrams for various alloys can be utilized. A large variety of combination alloys, for example, $M_{x1}M_{x2}M_{x3}MT_{y1}MT_{y2}MT_{y3}REO_x$ can be utilized, wherein the M series represents different metalloids, the MT series represent different transition metals, RE represents one or more rare earth elements, and O represents one or more oxides (other elements can be substituted for oxides). Magnetic properties are determined by the atomic structure, which can depend on the cooling rate used in forming the material, the chemical composition of the alloy, and subsequent treatment such as annealing temperature and/or time.

The method used to produce the amorphous microwires can provide differences in internal (residual) stresses and domain walls. The amorphous microwires can produce a magnetic field. When iron-rich alloys are utilized to produce the amorphous microwires, a domain wall propagation can be utilized to provide a magnetic field with the amorphous microwires. A vector turning can be utilized to tune or to provide a magnetic field. The addition of transition elements (e.g., Cr, Mo) can stabilize the amorphous structure. The amorphous alloys are designed to be soft magnetic materials. The composition of the alloys can be tailored to a particular application.

For some sensing applications, temperature stability of the amorphous microwires is desired. Short-range ordering can be modified by an annealing. Annealing can relax internal alloy stresses and induce temperature stability of the magnetic structure. Changing of magnetic parameters (e.g., Curie temp., magnetostriction, giant magnetoimpedance effect or GMI, anisotropy), can be accomplished by controlled annealing. For mechanical sensing applications, a tuning between the induced anisotropy and modifications in magnetostriction can be utilized. The desirable combination requires the optimization of the alloy composition and annealing conditions. Anisotropy can be induced after formation of the amorphous microwires by, for example, annealing in a magnetic field, Joule annealing, with or without tension applied to the microwires. Anisotropy can be circular or along a specific axis.

Materials with a high Curie temperature can be selected for high temperature measurements. For ambient temperature (~25° C.) or body temperature (~37° C.) measurements, lower-Curie temperature materials can be chosen. For example, greater addition of Cr or Ni, to microwires made of amorphous CoFe-based alloys, can have reduced Curie temperature and can be used for local temperate measurements. The impedance of a magnetic amorphous microwire can be measured by the voltage (V) change across a magnetic wire subjected to a high frequency current. Amorphous microwires can exhibit a large change in high-frequency impedance in the presence of a DC magnetic field, known as the magnetoimpedance (MI) effect or giant MI effect (GMI). The magnetic properties, which are selected and designed, can change with physical stress and temperature, causing changes in the impedance. By measuring or utilizing changes in impedence, the amorphous microwires can be utilized to measure and to send information. For example, a change in movement, a change in temperature, flow or pressure, or a change in conductivity can be measured by the amorphous magnetic microwires, and the information gathered by RF, conductive, light, or by inductive effects. Magnetoelastic interactions can determine the overall magnetic anisotropy energy, so stress-sensing magnetic mechanisms can be designed utilizing the amorphous microwires. If a coating is utilized, a change in refractive index of the coating can be determined by light or other electromagnetic radiation through the coating.

The coating can be applied during or after production of the microwire, for example, by passing the microwire through an extruder. The coating can include, for example, glass, metal or alloy, an oxide, borosilicate, PVC, polylactide, rubber, carbon, polysaccharide (e.g., alginate, fucoidans), peptides, polypeptides, proteins, glycoproteins, natural fiber, nucleotides, oligonucleotides, polynucleotides, nucleic acids, RNA, DNA, nylon, PEG, PTFE, a formulation for pharmaceutical delivery, or epoxy. The coating can have an average thickness in the range from about 1 μm to about 25 μm, about 1 μm to about 20 μm, about 1 μm to about 15 μm, about 1 μm to about 10 μm, about 1 μm to about 5 μm, about 2 μm to about 5 μm, or about about 1 μm to about 3 μm. Fiber optic properties can be designed in the coating, and light can be transmitted through the coating. One type of information can traverse in one direction through the coating while another type of information traverses in the opposite direction through the core microwire, for example. A coating can extend for a distance from a microwire without the microwire core, or the entire coating can contain a microwire core. In examples where a coating extends a distance from a microwire and the coating does not contain a microwire core, the extended coating can be utilized to extract a sample of cells or tissue from a subject, and the microwires can be utilized to easily removed the extract. A coating can include one or more therapeutics or active agents that can be released from the coating. The coating can include (or be substituted by) a targeting moiety, a binder, a surfactant, a stabilizer, a solubilizing agent, or functional groups, for example, to tailor applications. The coating can be a partial or complete layer of another metal or alloy. The microwires, without the coating, may have an average diameter in the range from about 1 micron to about 1 mm, about 1 μm to about 250 μm, about 1 μm to about 200 μm, about 1 μm to about 150 μm, about 1 μm to about 100 μm, about 1 μm to about 50 μm, or about 1 μm to about 30 μm.

Two or more layers of metal, the coating, or an entirely different alloy can be combined at least on a portion of the amorphous magnetic microwires. Some sensors can be formed by utilizing a thermocouple. An air or liquid (e.g., bodily fluid or breath) mass flow sensor can be formed by utilizing two or microwires, one to measure a change in flow temperature and another, for comparison, to measure ambient or environmental temperature. Another example of a mass flow sensor can pass a small current through a microwire with a known resistance and to measure a change in resistance, which will increase as temperature increases, thereby varying current flowing through the wire at constant voltage. By combining two or more microwires, mass flow can be detected at varying depths within an artery or passage. An accelerometer can be produced by measuring deflection of the damped mass of a portion of a microwire (e.g., an extension of a microwire into an artery). If the accelerometer experiences an acceleration, the mass is moved, causing a deflection in the wire, which can be measured by an adjacent microwire. The system is damped by the physical coherence of the microwires, so that large movements or oscillations of the extending wire coherence (mass and spring) do not affect the needed measurements.

The frequency response can be tuned by the known damping, applied field, tension, and known resonance. The coating can be utilized to detect, for example, heartrate, pressure, frequency response, or temperature in conjunction with the microwire core. One or more LEDs can be applied to the coating as a light source external or internal to a subject. Actuators can be formed by utilizing two or more materials with different coefficients of linear thermal expansion, or by utilizing a change in magnetic field to attract or deflect a separate microwire. Similarly, deflection can be utilized to measure pressure or flow by measuring a change in resistance across a gap between two or more microwires. Information can be transferred to or from the sensors and actuators utilizing electricity, light, EMF, movement, sonic waves, or acceleration.

An example of the magnetic microwires having advantages over magnetic nanoparticles is in hyperthermic treatment of tumors. After injection or targeted positioning and under the application of AC magnetic fields, ultrasound or lower frequency sonication, or light, magnetic nanoparticles deliver thermal energy to surrounding tissue, raising the local temperature and causing tumor cell death. Hyperthermic treatment can involve raising the temperature of a tissue to about 40-45° C., 42-45° C. or higher. The amorphous magnetic microwires do not incur the expensive synthesis and complex recovery issues of nanoparticles. Amorphous magnetic microwires can have features such as Hopkinson effect, magnetic softness, magnetic bistability, large MI (GMI) effect, and fast domain wall propagation. The toxic effects due to accumulation in body organs and biocompatibility problems are reduced or eliminated compared to nanoparticles. Compared to nanoparticles, magnetic microwires can accomplish the same local delivery of thermal energy under AC magnetic field stimulation, but have the significant advantage that they are microscale, not nanoscale. This feature allows magnetic microwires to generate a greater degree of localized thermal energy, whereby a higher temperature may be used due to better localization, as well as allowing them to be removable. This hyperthermia effect does not require current to flow through the magnetic microwires, so non-invasive treatment can be applied. A near instantaneous heating effect can be accomplished by application of laser light. The wavelength can be selected so as to not damage tissue and to apply nearly instant heat to the microwires. Application of an AC magnetic field can be utilized, which can be accomplished using a magnetic field generating device outside of a body in which magnetic microwires are implanted. Ultrasound (US) can be applied to cause US-induced heating by utilizing the magnetic microwires as sonosensitizers, which can enhance the thermal effect of US on the tissue by increasing US absorption. Magnetic losses in an alternating magnetic field can be utilized for heating due to different processes of magnetization reversal in the particle system, for example, hysteresis, Néel or Brown relaxation, and frictional losses.

A cancer treatment agent can be included in a coating on one or more microwires. Microwires with cancer treatment can be tested in vitro by applying an alternating magnetic field to measure heat loss and to analyze their specific absorption rate. Release of the treatment can be tailored using feedback information gathered from the microwire or the coating on a different microwire or the same. After the magnetic microwires are positioned at or near a treatment area, the treatment agent can be released by heating the microwires using applied energy, laser, electromagnetic field or US. Combinations of agents can be released from the same microwire or from a combination of different microwires. Example alloys for the microwires are CoFeSiB, CoMnSiB, CoFeSiBCrNi, and combinations with added rare earth elements. The microwires for hyperthermia (with electromagnetic field) can have large well defined anisotropy, soft magnetic properties, and negative magnetostriction. The alloys can have high magnetization saturation and low coercivity. Examples of cancer agents that can be released from a microwire are bleomycin, etoposide, cisplatin, epirubicin, cisplatin, 5-fluorouracil, capecitabine, methotrexate, cyclophosphamide, vinorelbine, folinic acid, oxaliplatincyclophosphamide, methotrexate, doxorubicin, docetaxel, vinblastine, dacarbazine, mustine, vincristine, radiation therapy agents, procarbazine, and prednisolone. The release can be controlled by the applied energy to the amorphous microwire causing a release, chemical, or solubility effect on the coating. After the treatments, the microwires can be removed from the treatment area. Magnetic microwires may be used in similar applications as magnetic nanoparticles but can offer the advantage of recoverability, i.e., they can be removed from the body, unlike magnetic nanoparticles which cannot be removed from the body once they are introduced.

By utilizing information transfer to and from the microwires, a treatment can involve both therapeutic and diagnostic aspects. For example, the microwires can be utilized by providing two or more types of amorphous microwires for treatments. One type can include an imaging agent and another can include a therapeutic agent. A cytotoxic radionuclide can be substituted for a known imaging metal or radiometal. As discussed above, a large variety of therapeutic agents or drugs can be provided with a coating on the amorphous microwires. After (or before) release of the therapeutic agent, the imaging agent can be released to assess effectiveness of treatment. Passive or active accumulation of nanoparticles at tumor sites occurs through permeability and retention at target sites, with containment issues. Utilizing magnetic microwires, the biodistribution is favorably enhanced to improve both the therapeutic effect and the imaging effect. To add targeting for a specific cellular receptor or other molecular feature of a diseased tissue, ligands can be conjugated to the microwires. The ligands can be, for example, organic molecules, monoclonal antibodies, aptamers, peptides, proteins, nucleotides, or other targeting materials. Imaging capabilities can be added to a microwire by conjugation of agents for detection, such as radionuclides or superparamagnetic (or paramagnetic) metals. Instead of slowing or halting growth of cells or tissue, any of the features above can be utilized to enhance growth of cells or tissue or to treat other conditions.

The amorphous microwires have penetrative advantages. Unlike nanoparticles, the amorphous magnetic microwires can be inserted through the walls of arteries and veins for diagnostic and treatment purposes. For example, a microwire can be inserted into an artery to measure flow or pressure through the artery and degree of atherosclerotic plaque. Acute condition such as angina can be detected before acute pain occurs. Information diagnostic to the condition can be transferred from the interior of the artery to another location either internal or external to the patient. Based on the diagnostic information, release of a therapeutic agent can be triggered from another microwire adjacent to the diagnostic microwire (or upstream from the diagnostic microwire). The therapeutic agent can be a vasodilator released in response to increased pressure (or decreased flow). The therapeutic agent can be released from a coating on the microwire. Examples of therapeutic agents are ranolazine, nitrates, clot-preventing drugs, beta blockers, statins, calcium channel blockers, and blood pressure-lowering medications. A stent can be utilized to position microwires. The penetrative advantages can be utilized for other sensitive conditions or organs with further examples including stroke prevention, brain injury diagnosis, liver diagnosis, and probing into muscles or adipose. The physical stability and strength of the microwires enables penetration from outside a patient for diagnostic and treatment, with easy removal. The great flexibility of the microwires allows long-term implantation if desired. Diagnostic and treatment information, over time, provided within a patient can be transferred by the microwires to an implanted information storage device including RAM, software and a processor. An implantable medical device can be in one location of a subject (e.g., adipose) with the microwires at a sensitive location (e.g., artery, nervous system, heart). The amorphous magnetic microwires can provide energy-transporting and information-transporting biomedical applications to an electrode, a tissue heating element, a neural probe, a neural stimulator, a biosensor, a catheter, a vascular theranostic, or a microprocessor. The amorphous microwires can provide a probe within a patient even in sensitive locations (e.g., central nervous system), with information transferred from the sensitive location to a storage/diagnostic location. Information transfer can extend for long distances in a patient from head to toe.

A plurality of locations in a patient can be monitored and treated simultaneously with the amorphous magnetic microwires. Meningitis of the protective membranes covering the brain and spinal cord, can be detected by increased cerebrospinal pressure/analysis. A bacterial or viral infection of the fluid surrounding the brain and spinal cord can cause the swelling. However, injuries, cancer, and therapeutics can cause meningitis. The microwires herein can be utilized to transfer information through the meninges while an infection, cancer, or injury is being treated. The microwires can be utilized to penetrate deep into neural tissue with little or no damage to surrounding tissue. A method of treating a condition in a subject can include implanting one or more magnetic microwires into the subject; applying US, laser, electromagnetic radiation, or an AC magnetic field to the microwire, whereby the microwire heats. Diagnostic feedback can be obtained there through a separate implant, microwire, or application, and the first method can be changed during treatment based on the feedback.

Figure 14:
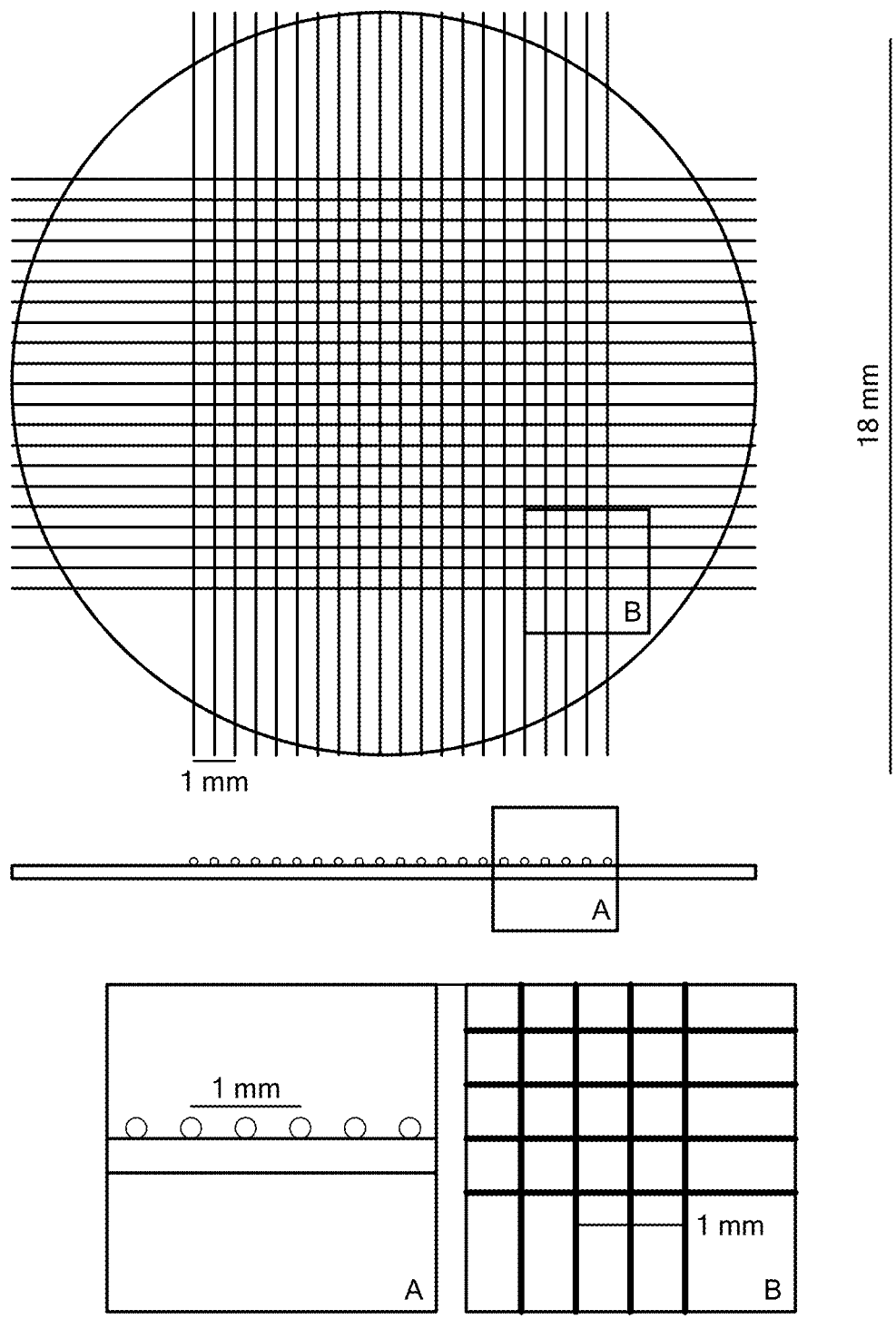
FIG. 14 illustrates a design of microwire mesh spacing on a Pyrex cover glass. Inset A is a side-view enlargement of the microwires on the Pyrex cover glass. Inset B is a top-view enlargement of the microwire mesh. The scale bar at far right is 18 mm. The scale bars shown in insets A and B are 1 mm.
Figures 15A, 15B, 15C:
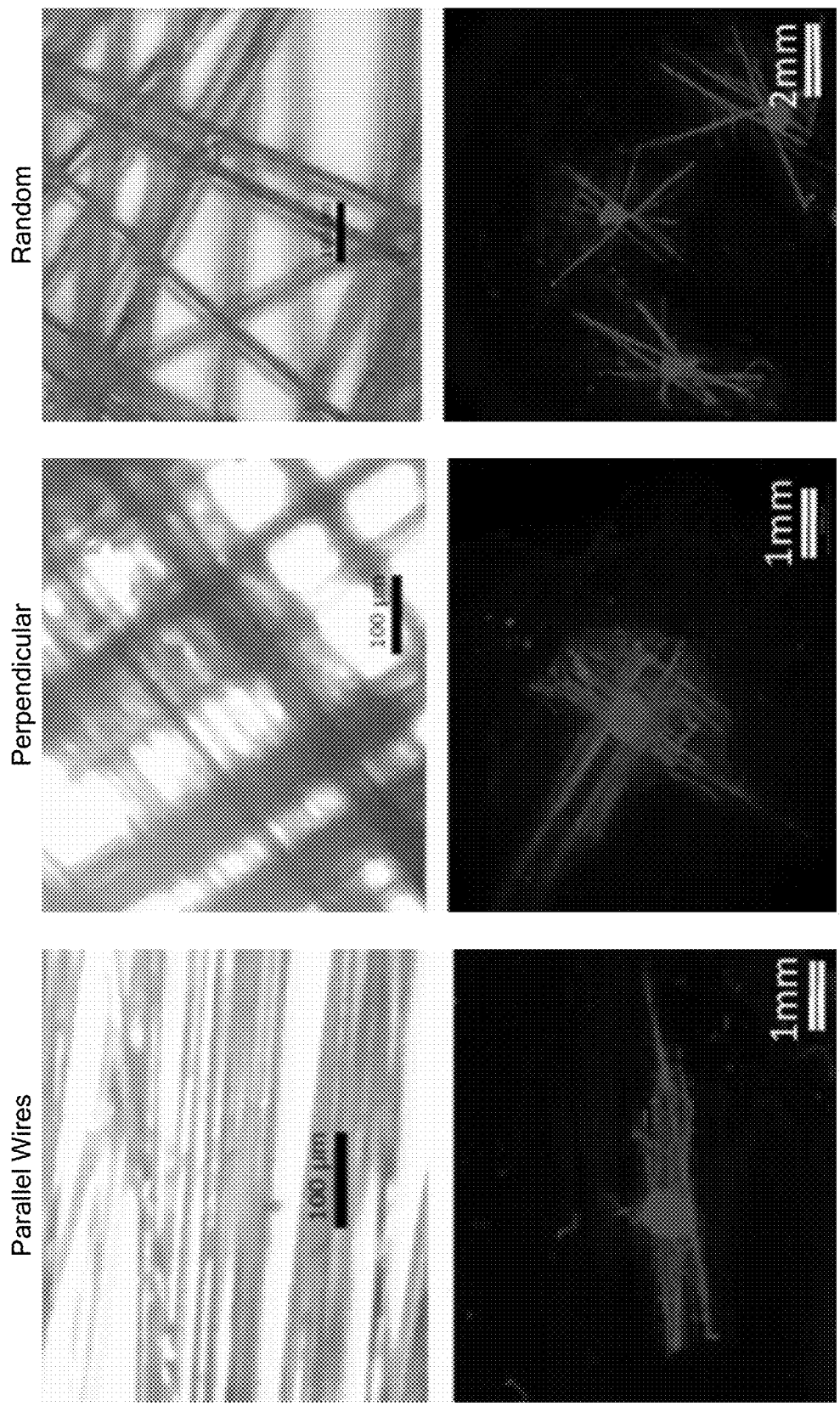
FIG. 15A shows a photo of parallel microwires (top, scale bar=100 microns) and a fluorescence microscope image of DRG outgrowth on parallel microwires (bottom, scale bar=1 mm).
FIG. 15B shows a photo of perpendicular microwires in a mesh (top, scale bar=100 microns) and a fluorescence microscope image of DRG outgrowth on perpendicular microwires (bottom, scale bar=1 mm).
FIG. 15C shows a photo of randomly positioned microwires (top, scale bar=100 microns) and a fluorescence microscope image of DRG outgrowth on randomly positioned microwires (bottom, scale bar=2 mm).

The microwires provided herein can be utilized to direct nerve growth and to increase length of nerve growth. The microwires can be positioned with a parallel spacing between microwires to steer neurite growth along the length of the microwires. A microwire mesh spacing design is illustrated in FIG. 14, showing about 1 mm (insets A and B) spanning across three microwires. Glass coated magnetic microwires ($Fe_{80}Si_{10}B_{10}$ core) are shown in parallel arrangement, perpendicular arrangement, and random arrangement in FIG. 15A (top), FIG. 15B (top), and FIG. 15C (top), respectively. DRG growing with stained neurites on the glass coated magnetic microwires follow the wires without application of an external magnetic field as is shown at the bottom of FIG. 15A, FIG. 15B, and FIG. 15C.

For directing growth, the spacing between two microwires can be described as a ratio of the overall diameter of the microwire:the space between adjacent microwires. A microwire with an average diameter of 50 microns may have a space between the microwire and an adjacent microwire of about 250 microns, so the ratio would be about 50:250 or 1:5. For example, the space between two or more microwires can be in the range from about 1× to about 10×, from about 1× to about 5×, from about 2× to about 5×, or from about 3× to about 5× the average diameter of the two or more microwires.

A magnetic field can be applied to neurons growing with the microwires to enhance growth. The magnetic field can be applied constantly or at intervals. The magnetic field can arise from the microwires themselves or be induced in the microwires using an external source. The magnetic field can be in the range from about 30 gauss to about 25000 gauss (2.5 T), from about 60 gauss to about 2 T, from about 100 gauss to about 1 T, from about 100 gauss to about 5000 gauss, or from about 100 gauss to about 1000 gauss, or from about 100 gauss to about 15000 gauss. The magnetic field can be an alternating magnetic field of a stable or changing (e.g., alternating) frequency, or a direct magnetic field. The magnetic field can be utilized to induce an electric current in the microwires.

Figure 4A:
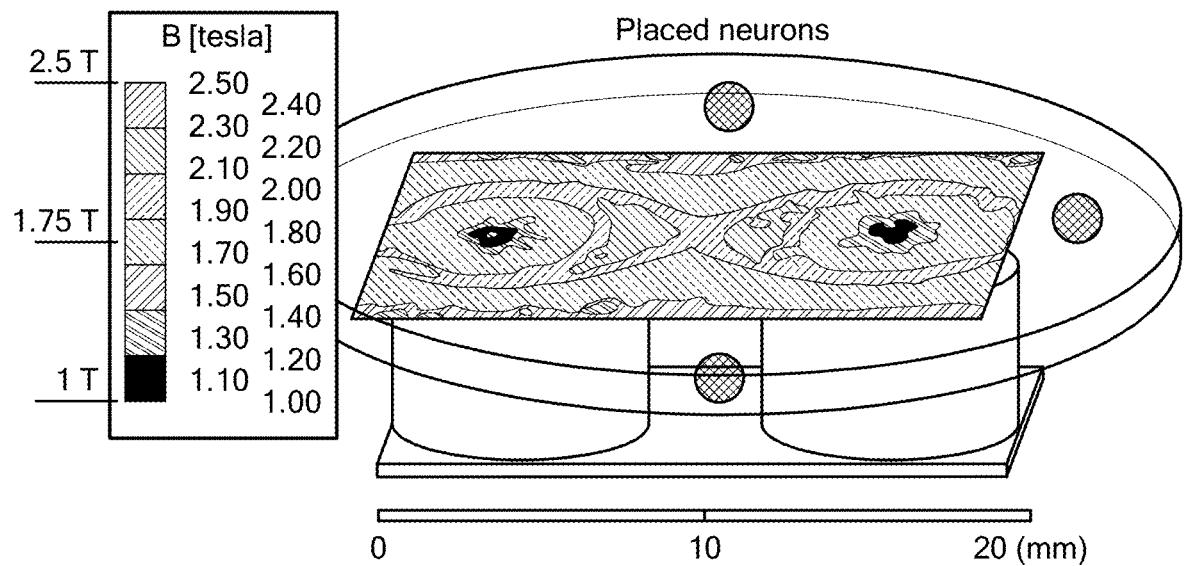
FIG. 4A shows an illustration of a magnetic apparatus and Ansys® software model of strength and field vectors. A cross-section of the magnetic setup is shown in FIG. 4B. The scale bar at the left of FIG. 4A indicates from 1-2.5 tesla. The scale bar at the bottom of FIG. 4A indicates a total length of 20 mm.
Figure 5A:
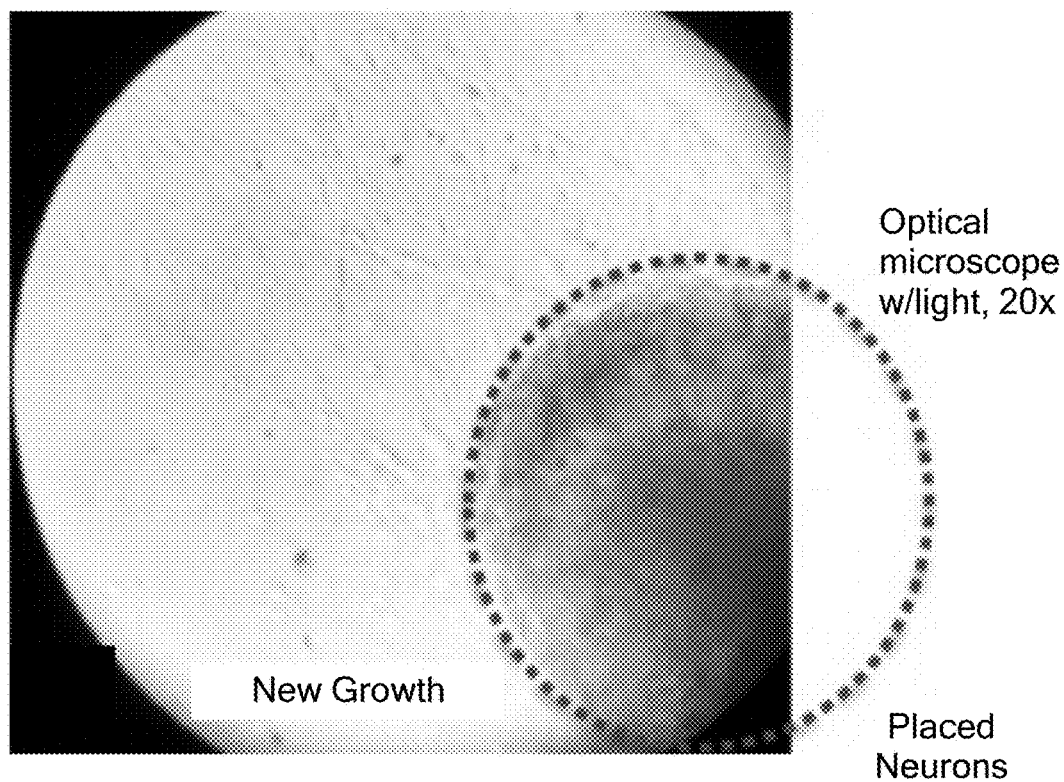
FIG. 5A shows an optical microscope image (20×) of rodent DRG neurons with new neurite growth, grown in a magnetic field.
Figure 5B:
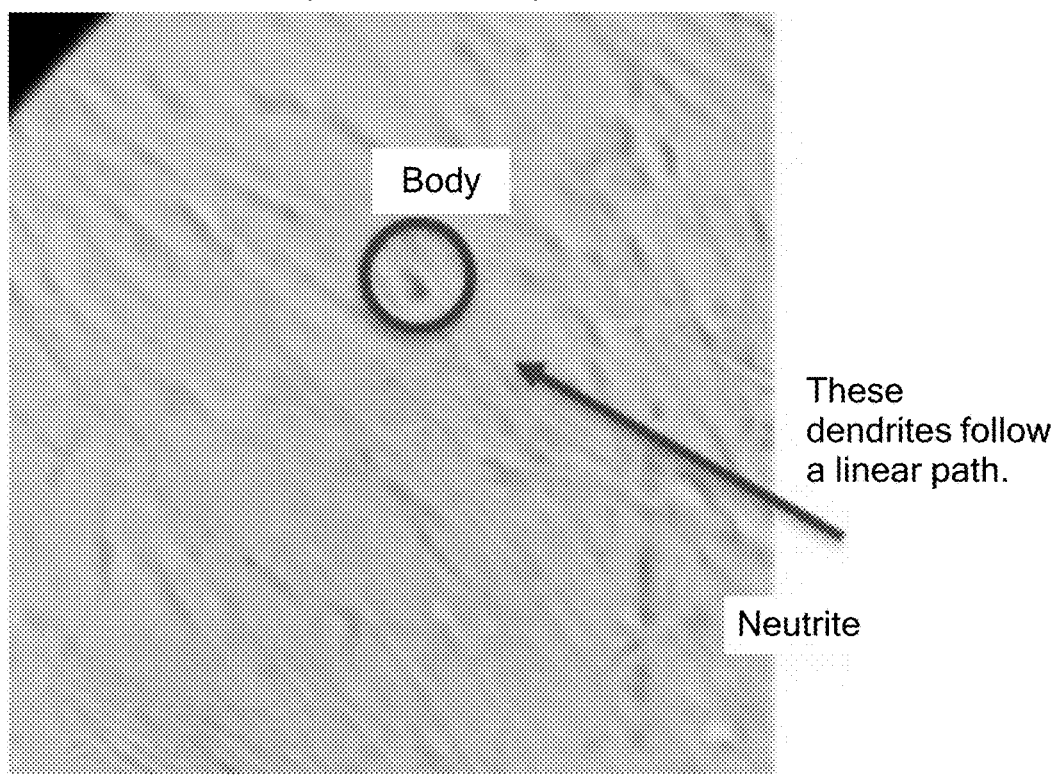
FIG. 5B shows an enlarged optical microscope image of FIG. 5A, enlarging the new neurite growth, grown in a magnetic field.
Figure 6A:
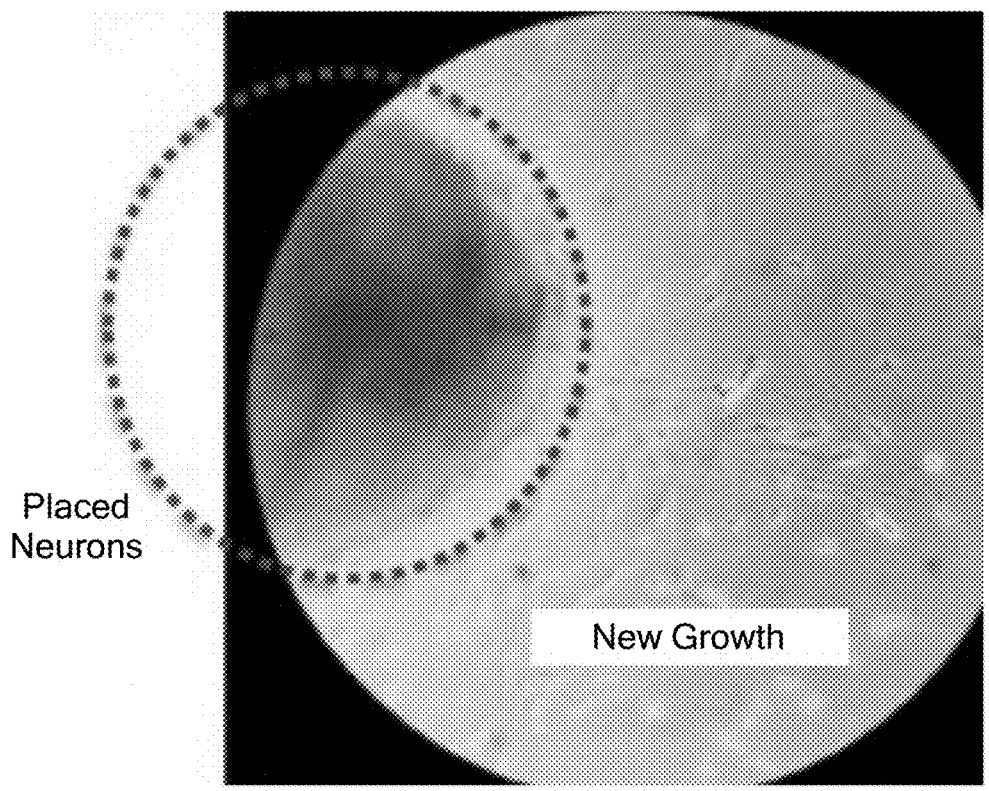
FIG. 6A shows an optical microscope image of DRG neurons with new neurite growth, grown without magnetic field.
Figure 6B:
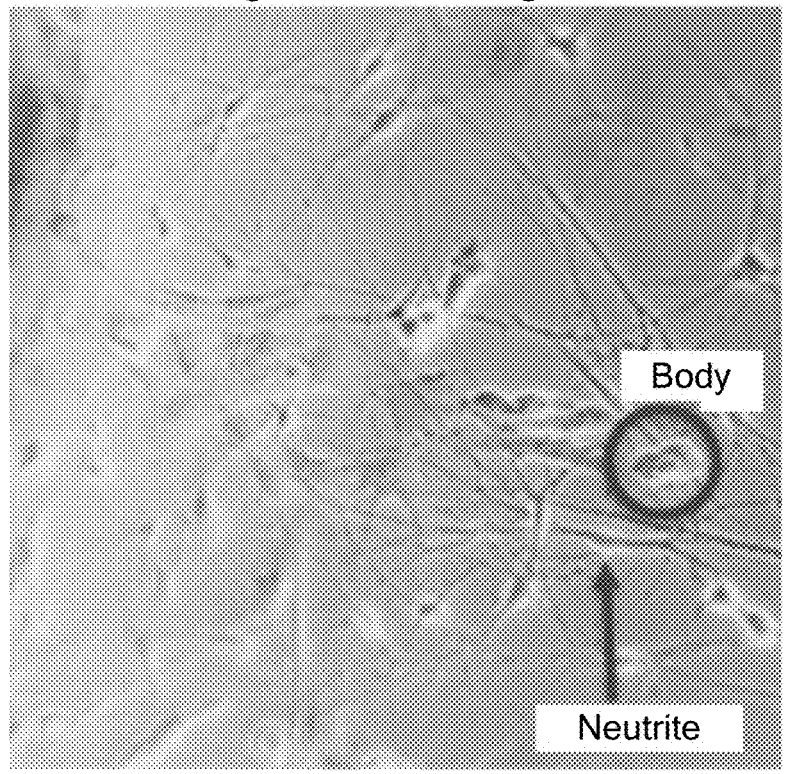
FIG. 6B shows an enlargement from FIG. 6A, showing the new neurite growth, grown without magnetic field.

FIG. 4A shows an apparatus that can apply a magnetic field in the range from about 1 T to about 2.5 T to growing neurons. FIG. 5A shows an optical micrograph of neurons growing neurites (new growth) in a magnetic field with the apparatus and without microwires. In FIG. 5B, which is an enlarged view of FIG. 5A, the growing neurites follow a linear path. Neurons grown without application of the magnetic field are shown in FIG. 6A and in FIG. 6B. As seen in FIG. 6B, the neurites grow without the directionality that is observed in FIG. 5B.

The microwires can be configured in an implantable medical device including a single microwire, or two or more microwires arranged into a pattern, such as a pattern of parallel microwires. The two or more microwires can be positioned to contact the ends of damaged nerves with the microwires spanning a gap or an injury between the damaged nerves. For example, the gap or injury can be in the range from about 1 mm to about 12 cm. A magnetic field can be applied to the microwires. The damaged nerves can be contacted with a growth enhancer. For example, the microwires can be coated with the growth enhancer. Examples of growth enhancers are nerve growth factor (NGF), retinoic acid, laminin, 6-aminonicotinamde, poly(vinyl alcohol), poly-(D or L)-lactide, polyurethane acrylate, polycaprolactone, Schwann cells, stem cells, plasma, an antibiotic, poly (3,4-ethylenedioxythiophene) polystyrene sulfonate, an amino acid, a peptide, a protein, or a combination thereof. The growth enhancers can be combined with other therapeutics described above with the same or with different microwires. As discussed above, the enhancers can be included in a coating and can have hyperthermic controlled release.

The microwires can include a coating that can conduct light, such as a glass coating. The light can include a wavelength in the range from about 190 nm to about 1000 nm. Light can be applied to the growing neurons through the light-conductive coating. The light can be applied constantly or at intervals. For example, a light source can be applied to a central region of the microwires. The light can conduct through the coating and direct to the neurons near the ends of the microwires. Light can be emitted from the coating along the length of the two or more microwires.

Figure 13:
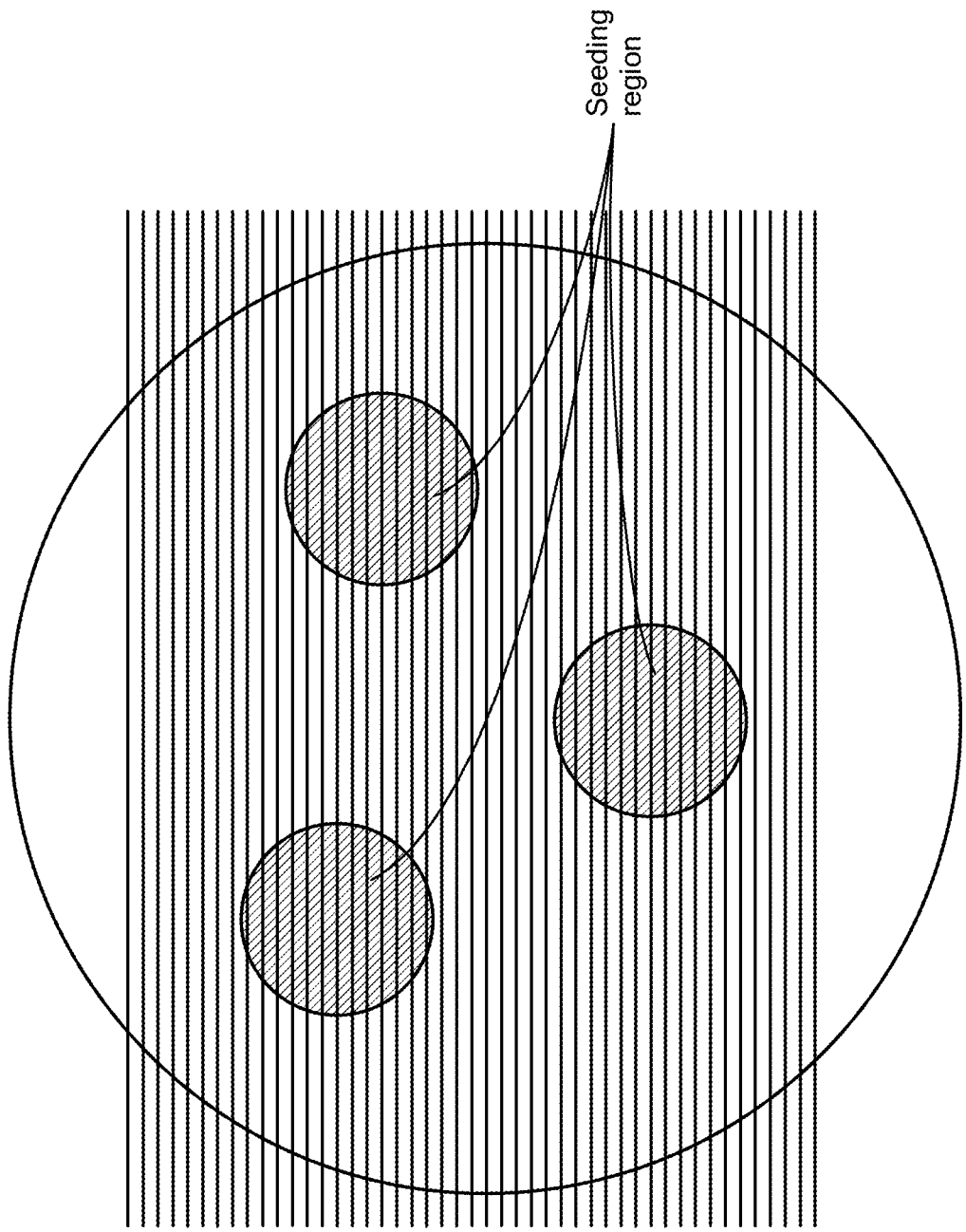
FIG. 13 is a diagram illustrating rodent DRG seeding areas (regions) on parallel-aligned wire mesh samples.
Figures 16A, 16B:
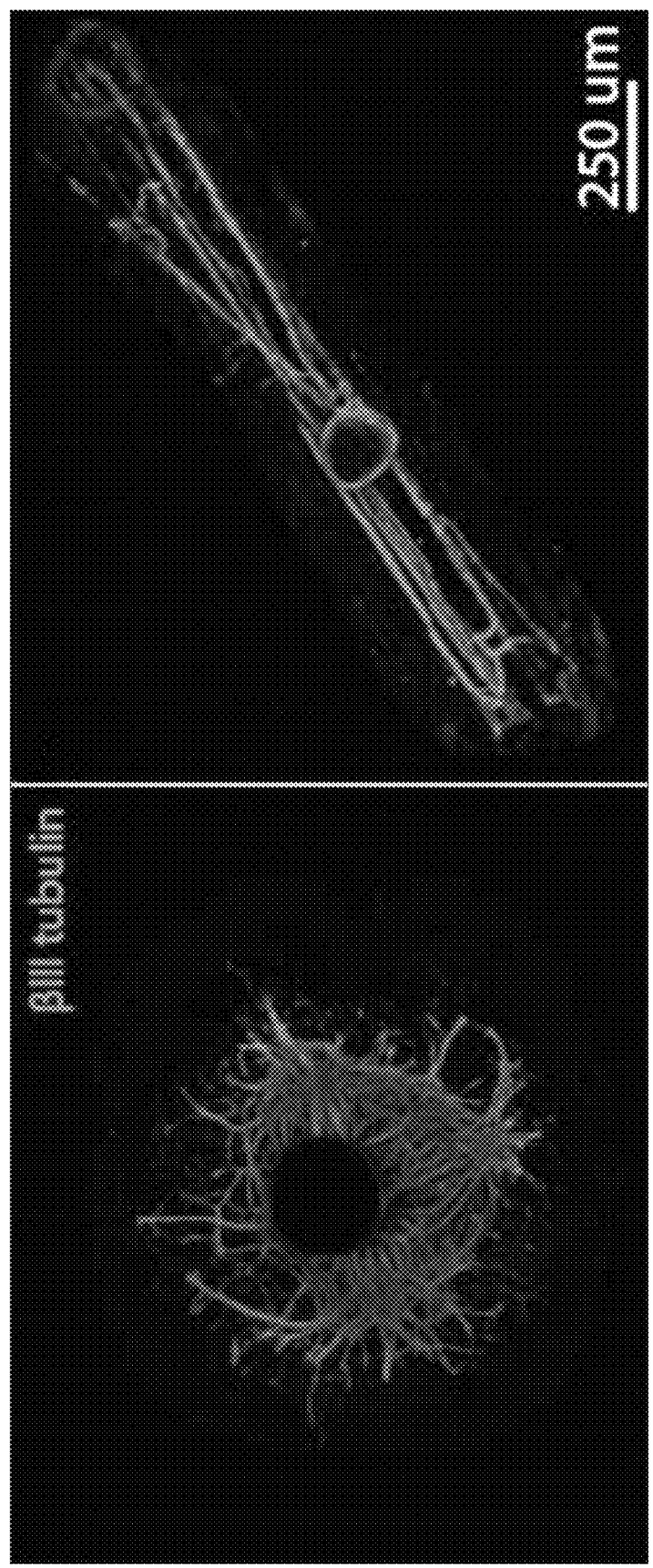
FIG. 16A shows a fluorescence microscope image of DRG outgrowth (control) grown without microwires. Staining is for beta-III tubulin. The scale bar shown in FIG. 16B (at lower right), for comparison, is 250 microns.
FIG. 16B shows a fluorescence microscope image of DRG outgrowth growth on parallel-aligned microwire mesh. Staining is for beta-III tubulin. The scale bar is 250 microns.
Figure 17A:
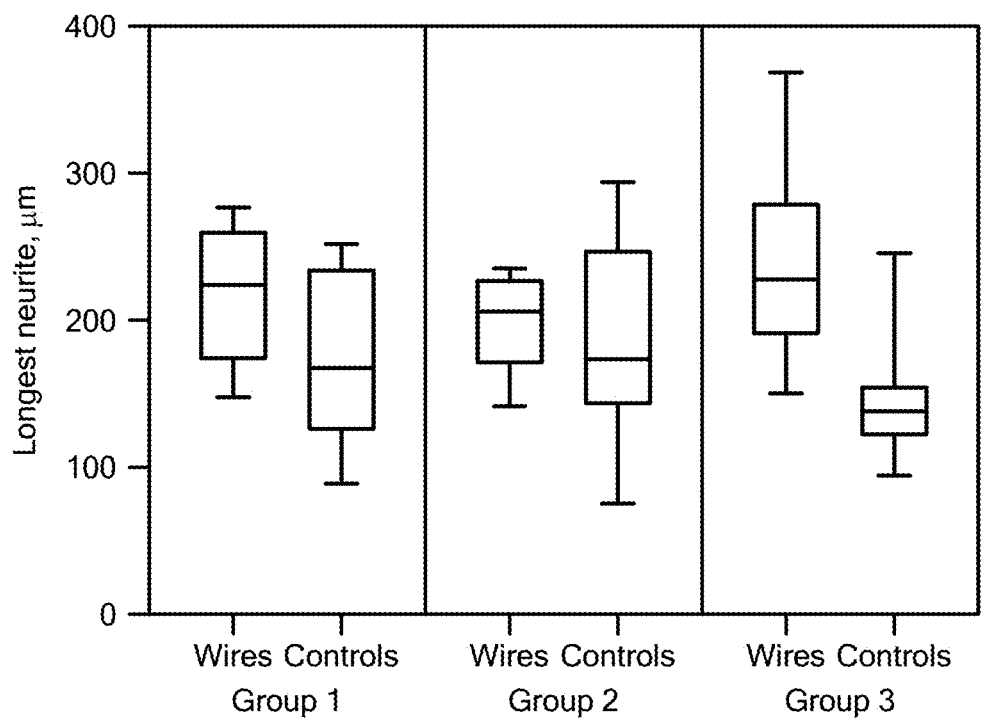
FIG. 17A shows box-and-whisker plots of longest neurite, in microns, versus growth condition for DRG Group 1, Group 2, and Group 3, grown in wire mesh and control.
Figure 17B:
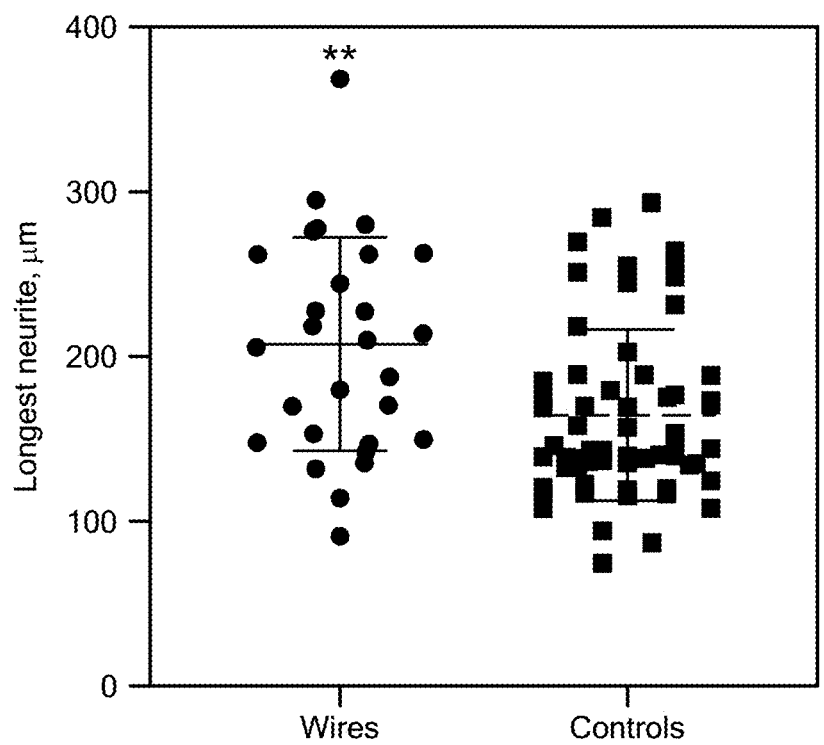
FIG. 17B shows pooled data from FIG. 17A (n=3) for longest neurite, in microns, grown in wire mesh and control conditions.

The present technology can surprisingly provide increased length in a growth (neurite) of a neuron aligned along the topographical growth of the microwires. FIG. 13 shows seeding areas for DRG on a flat array of parallel arranged microwires. Neurites growing on the microwires grow with alignment along the lengths of the microwires as shown in the microscope image of FIG. 16B. The longest calculated neurite grown is compared between wire grown samples and control DRG in FIG. 17A. Longest achieved neurite is improved in all three experimental groups, Group 1, Group 2, and Group 3 (Wires) on wire mesh. The first experimental group has a 17% increase (219.6 μm±64.3 μm) in longest measured neurite (FIG. 17A, left). The second experimental group indicates a 39% increase (198.3 μm±29.6 μm) in longest neurite (FIG. 17A, center). The third experimental group measures a 38.7% increase (240.5 μm±87.8 μm) in longest neurite (FIG. 17A, right). With data across all experimental groups pooled (FIG. 17B), longest neurite seen in wire mesh samples is different than control (p=0.020). FIG. 17B shows pooled data (n=3) for wire meshes compared to control neurite length.

The peripheral nervous system has mild regenerative properties, and can bridge gaps up to 3 cm under ideal conditions (Schmidt, C E; Leach, J B, 2003). The present technology can provide further increased length of neuronal growth, so as to traverse a gap induced by a cut or wound resulting in a severed nerve, and to promote growth and reestablishment of neuronal signaling across the gap. The microwires can be readily removed after providing aligned and increased growth, leaving behind the healed nerve growth.

EXAMPLES

Example 1: Production of Amorphous Microwires

Magnetically conductive amorphous microwires were fabricated through a combination of stretching and rapid solidification. This was done by melting the metal or alloy and then rapidly cooling it back into a solid phase to prevent the constituent atoms from returning to low-energy crystalline structure, for example, with an in-water quenching process. The typical alloy that was generated from this process is thermodynamically metastable, with compositions of the $M_xMT_y$ form, where MT is a transition metal and M is a metalloid. The manufactured alloys included iron, silicon, and boron, creating an iron-borosilicate metallic glass alloy. For glass coating, this alloy was then placed on a drawing device for glass coating utilizing a Taylor-Ulitovski process, which can create amorphous ferromagnetic wires with a glass coating.

Glass coating of the microwires was performed by placing the metal alloy in a Pyrex glass capillary with a tapered end, surrounded by an AC current induction coil, which melts the alloy and surrounding glass. The melted glass-encased alloy was then pulled, quenched with water, and drawn into wire by a bobbin system. The drawing system allows for varied diameter of the inner core and glass coating, which creates wire with specific magnetic properties. The drawn wire was then spooled for storage and use. Water-quenched magnetic microwires, without coating, were also produced.

Example 2: Positioning of Amorphous Microwires

Figure 10A:
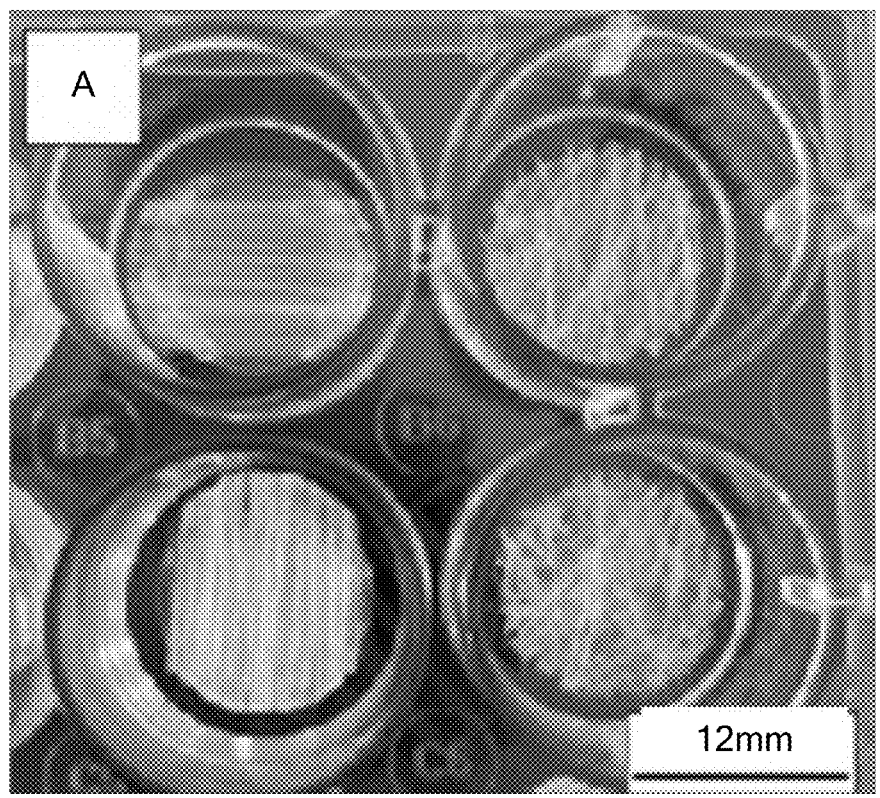
FIG. 10A shows a photograph of parallel-aligned and randomly placed microwire meshes. The scale bar is 12 mm.
Figure 10B:
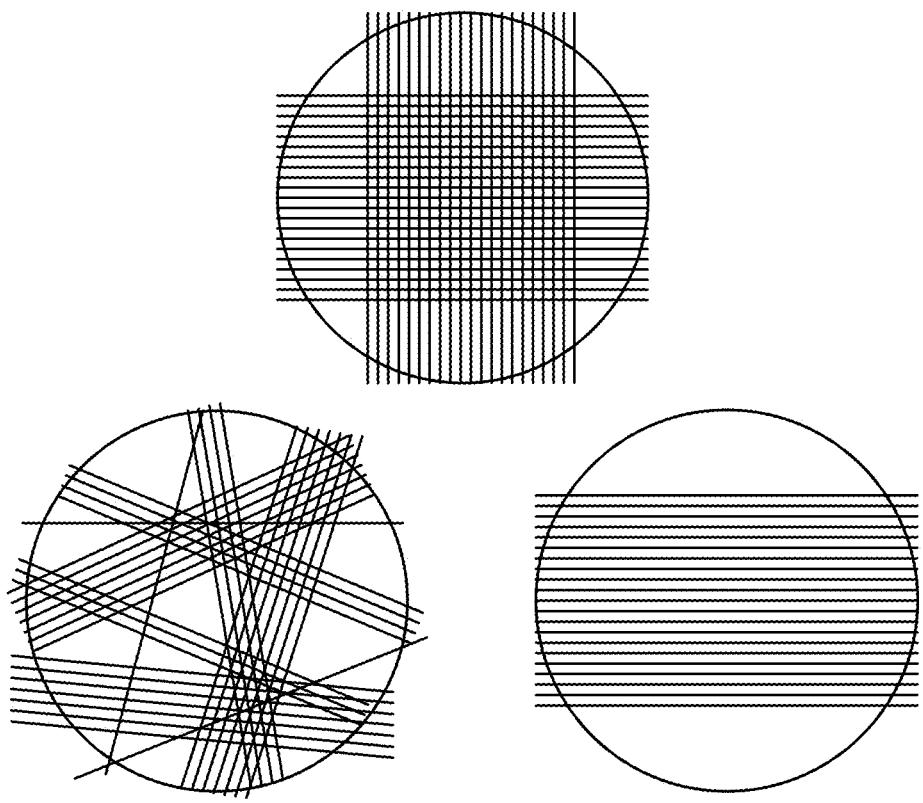
FIG. 10B shows a schematic of randomly placed microwires, parallel-aligned microwires, and orthogonally aligned microwires (or microwire mesh).

Amorphous microwires were initially assembled and positioned by hand, beginning by cutting spools of magnetic microwire or physically identical fiber optic glass wire (ThorLabs) to 3 cm pieces. Glass coverslips were coated with nail polish around the rim to adhere the wires, and wire was then placed across the coverslip. Wire pieces were placed in either parallel or perpendicular meshes of varying mesh densities and allowed to dry overnight. Initial lots of wire mesh samples are shown in FIG. 10A, which shows a photograph of parallel-aligned and randomly placed wire meshes (scale bar=12 mm). FIG. 10B shows a schematic of all three types of wire meshes. A second layer of nail polish was applied to ensure wire attachment and allowed to dry for another hour. Once dry, the positioned wire samples were treated on the glass coverslips, sterilized, and coated in laminin.

The initial wire samples assembled on the glass coverslips as described above were cleaned using Tergazyme (Alconox, 10 mg/mL) overnight. However, this cleaning procedure destroyed the integrity of the nail polish. Positioned wire samples were also prepared with super glue gel (Gorilla Tough super glue), but these also failed to hold the wires after cleaning. To combat this issue, a new wire assembly protocol was developed. At this time, the mesh density of the wires (ratio of wire diameter:space between wire) was also determined to be too high, so this was also considered when developing a new protocol (FIG. 11).

Figure 11:
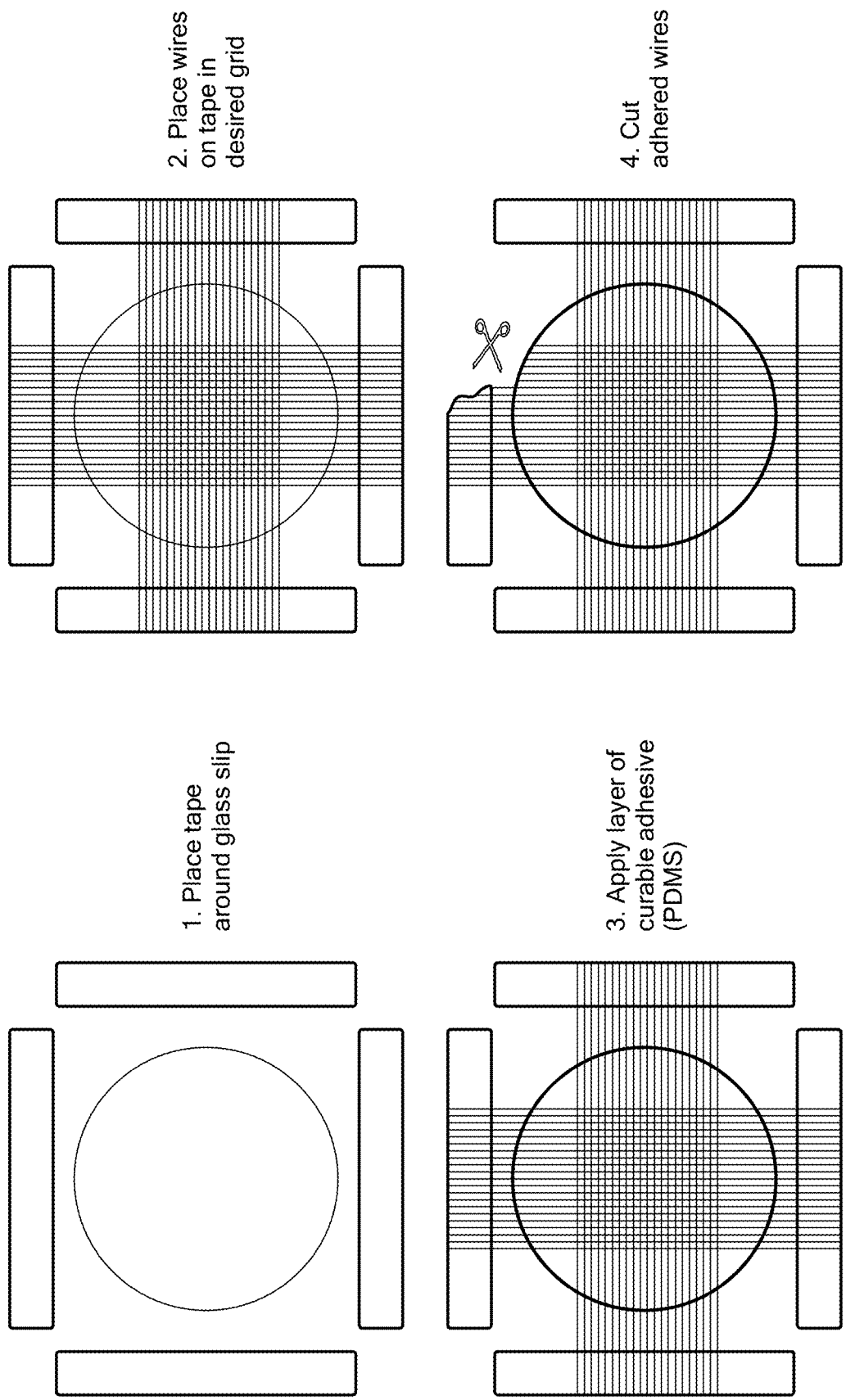
FIG. 11 shows an illustration of a four-step procedure for assembly of a microwire mesh.

FIG. 11 shows a schematic of a redesigned wire mesh assembly process to enhance mesh reusability. Wire mesh is assembled in a four-step process by placing tape around the glass cover slip, taping down wires in the desired grid shape, and applying a silicon adhesive.

Wires were assembled using polydimethylsiloxane (PDMS) (SYLGARD, Dow Corning), a silicon-based organic polymer, which would allow for washing and sterilizing without compromising the mesh, to enable re-usability. Additionally, it was at this time that the mesh density was reduced to 1:5. For example, a space between two wires was about 5 times the diameter of the wires. Wire samples were assembled with forceps under a Zeiss optical dissection microscope. The samples, once coated in PDMS, were placed under desiccation at room temperature to eliminate air bubbles, and then placed in a vacuum oven at 5 mmHg and 50° C. to cure overnight.

Figure 12A:
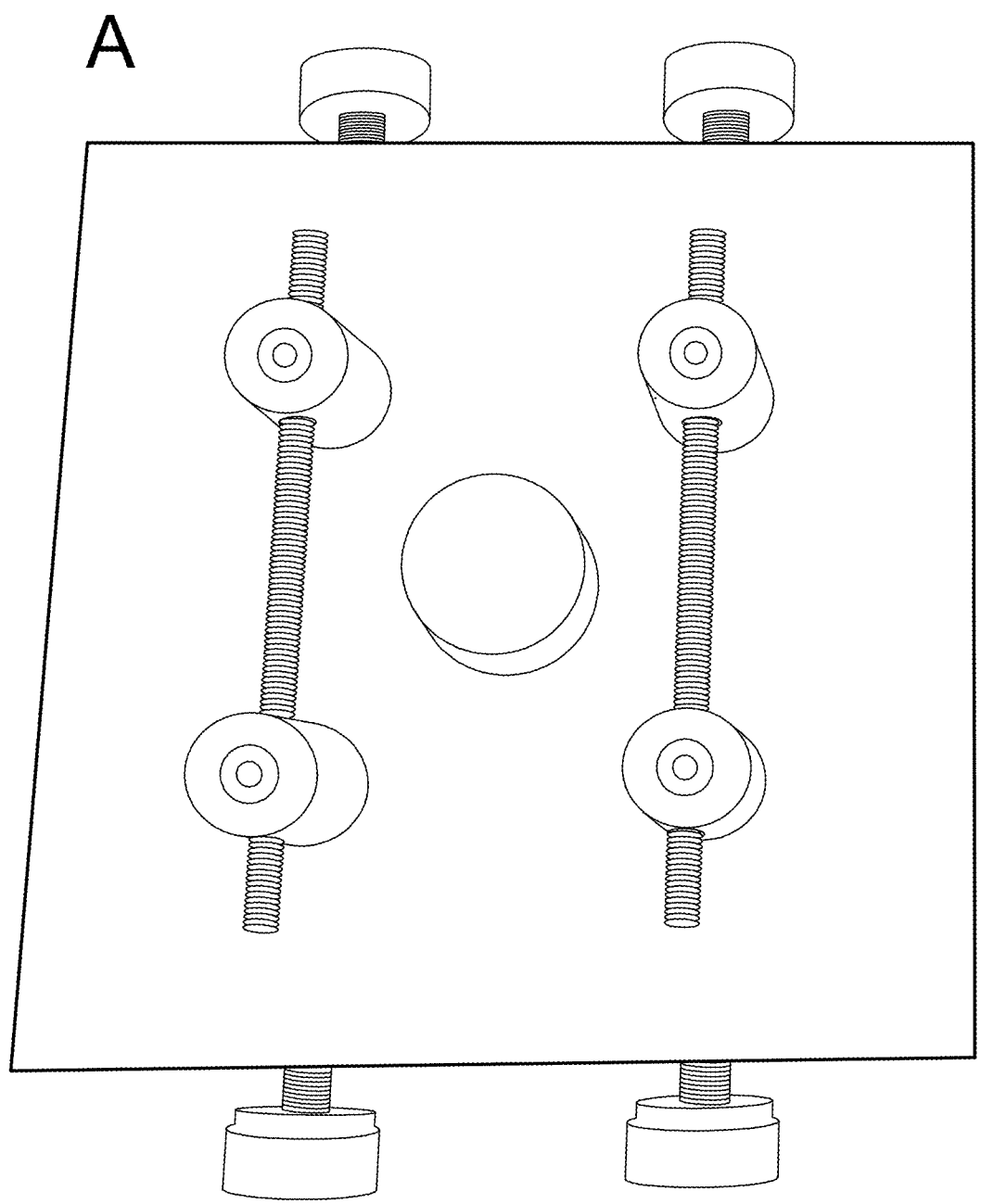
FIG. 12A shows an assembly tool for assembling parallel-aligned microwires and microwire mesh. Two threaded rods are secured left and right of a central pedestal. The black scale bar shown at lower right is 2.5 cm.
Figure 12B:
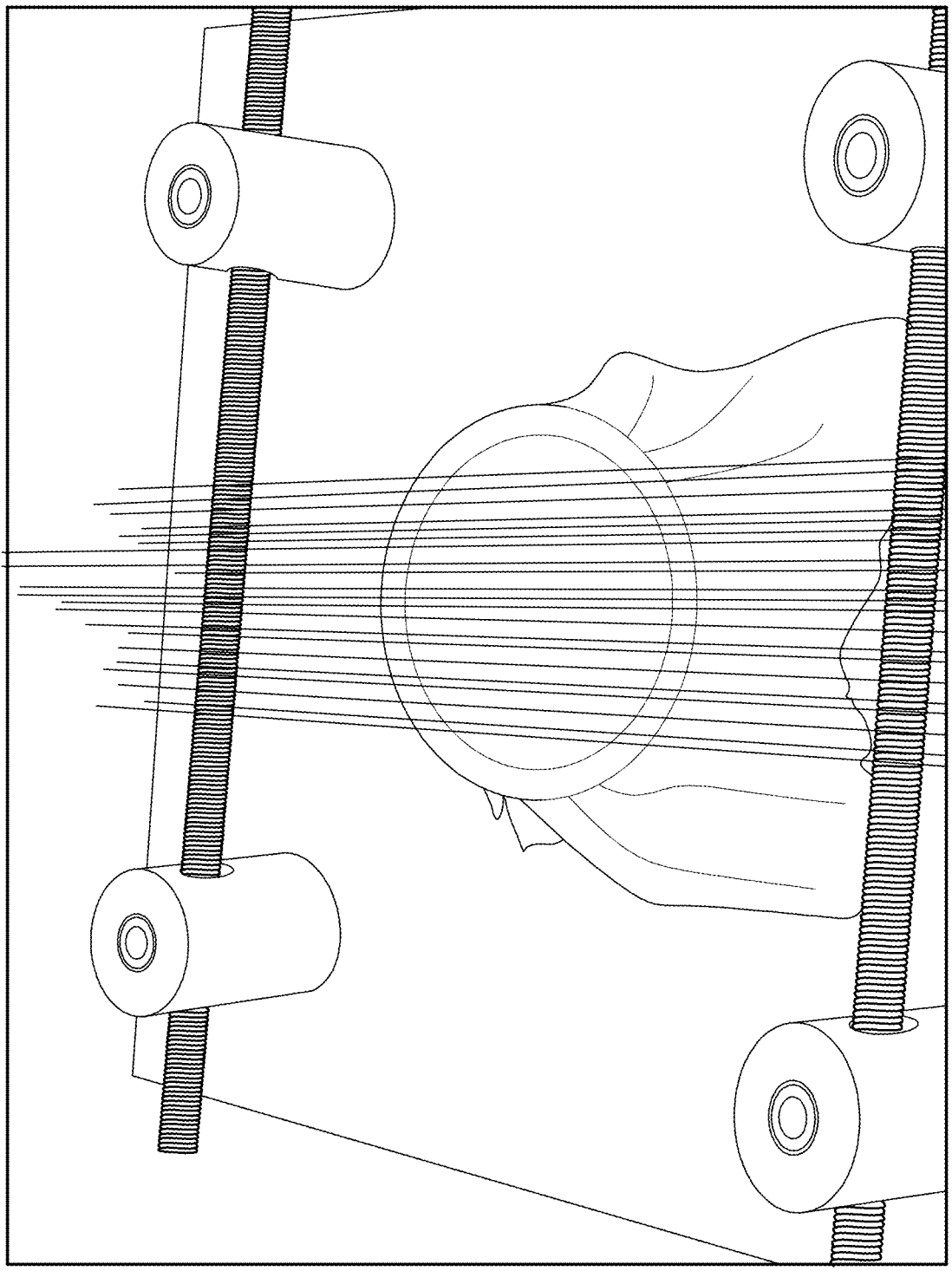
FIG. 12B shows the assembly tool of FIG. 12A in use, with microwires placed in the spacing threads and adhered in place. The central pedestal is protected with parafilm.

To further improve the reproducibility, a wire alignment device was designed and is shown in FIG. 12A and FIG. 12B. This device used two threaded bolts with deep grooves 250 μm apart. This allowed for wires to be placed within the grooves and would automatically set 50 μm-diameter wires at the desired 1:5 mesh density to enhance uniformity of the mesh. This apparatus included a pedestal to place the glass coverslip on, and adjustable heights for the threaded rods to help assemble the units. FIG. 12A and FIG. 12B show examples of the wire assembly tool fabricated. In FIG. 12B the assembly tool is in use, with parafilm protecting the pedestal, and glass wires adhered to the threaded bolts using nail polish. In FIG. 12A, the black scale bar at lower right is 2.5 cm.

Example 3: Growth of Rodent Dorsal Root Ganglia in Magnetic Fields

To determine how a magnetic field could influence extension of neurites in neurons from DRG, setups were constructed to subject the neurite outgrowth to a mild magnetic field (about $\mu_0 H$ up to about 500 Gauss). Two magnetic setups were designed and constructed to subject DRG to static magnetic fields of different magnitudes. The "Setup 1" shown at the top of FIG. 1 has two neodymium-iron-boron permanent magnet cylinders (McMaster Carr, N52, 1.6 mm thick×6.4 mm diameter) that are arranged in alternating north-south remanent magnetic polarization (along the thickness) configurations and placed 18 mm apart from axis to axis. An 18 mm scale bar is shown at the top of FIG. 1. The scale bar at the center of FIG. 1 is 10 mm. To create a closed magnetic flux path and to minimize the magnetic interference to other cell growth within the incubator, the magnet cylinder pair was bookended by two silicon steel plates (M-15 bare, 6.6 mm×28 mm×0.5 mm) for the flux closure.

Figure 2:
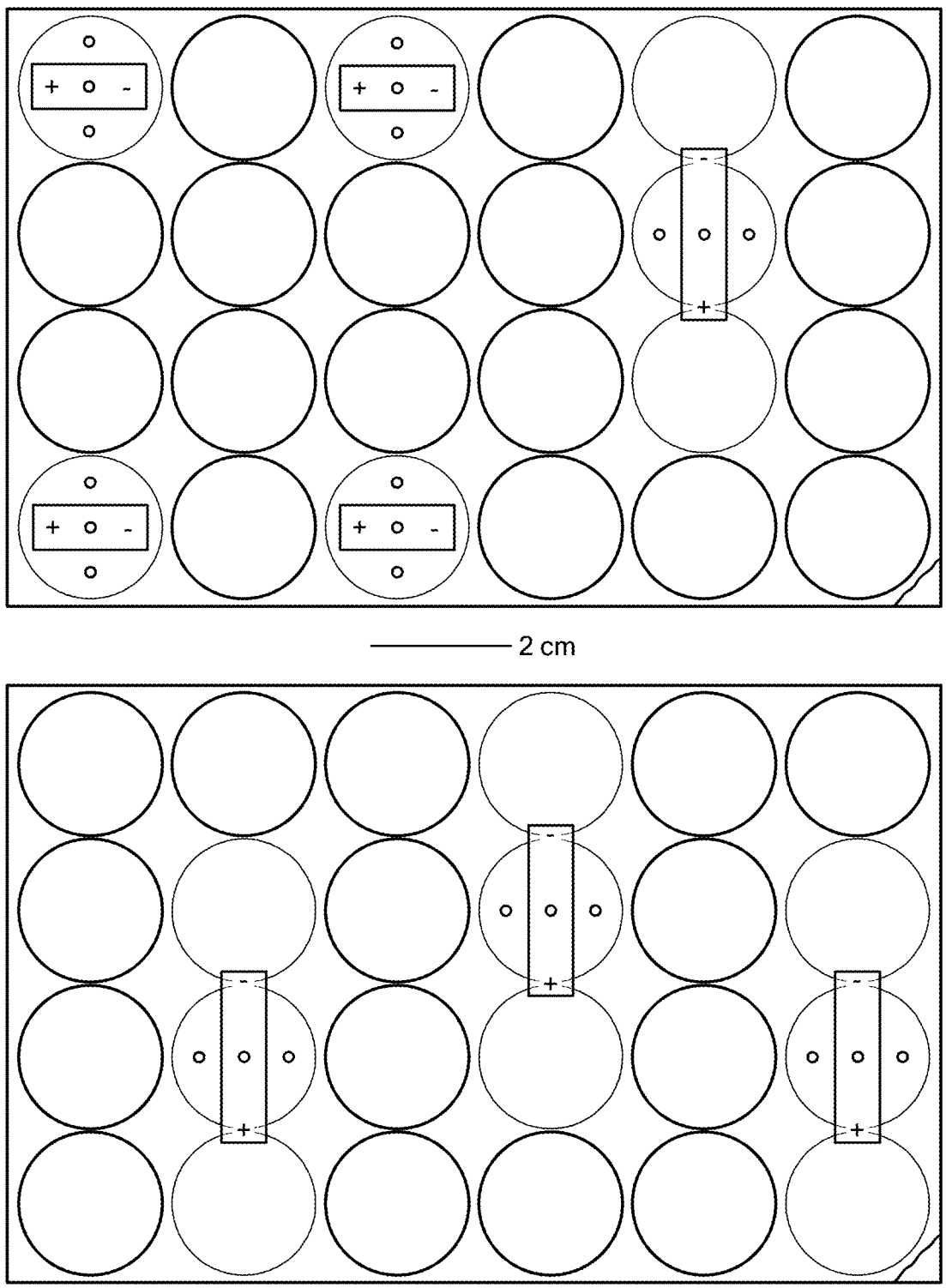
FIG. 2 at bottom shows an illustration of placement of 3 setups of magnetic setup 1 positioned under a 24-well culture plate. At the top of FIG. 2, four setups of magnetic setup 2 are positioned under a 24-well plate with one additional setup of magnetic setup 1 positioned under the 24-well plate at the top of FIG. 2. The scale bar at center is 2 cm.
Figures 3A, 3B:
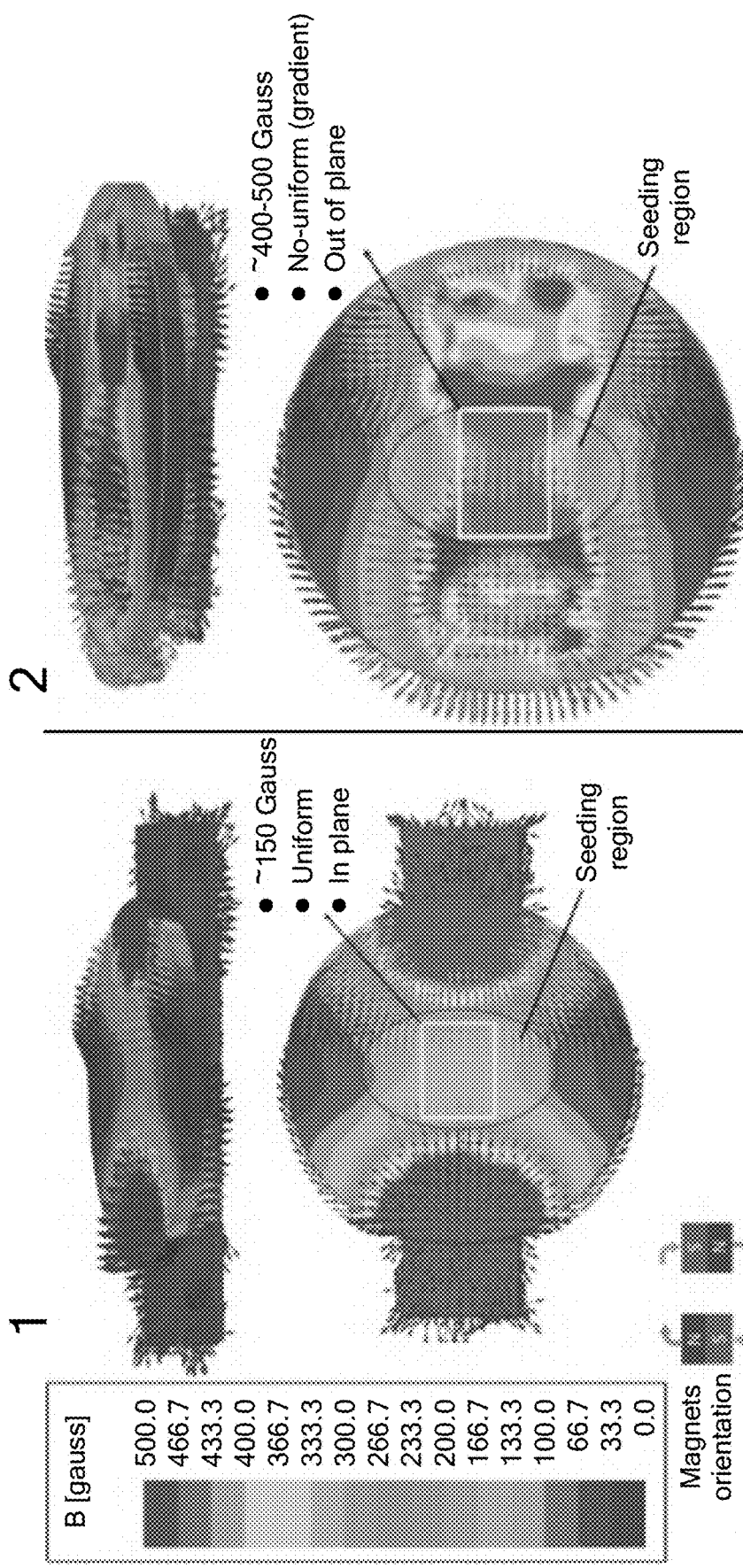
FIG. 3A shows an Ansys® software (electromagnetic package, Ansys® Electromagnetics Suite, ANSYS, Inc.) model of strength and field vectors of magnetic setup 1. The scale bar at left indicates from ~0-500 gauss.
FIG. 3B shows an Ansys® software model of strength and field vectors of magnetic setup 2. The scale bar at left of FIG. 3A indicates from ~0-500 gauss.

The "Setup 2" shown at the bottom of FIG. 1 has a similar configuration but utilizes a magnet pair with different size (1.6 mm thick×4.8 mm diameter) and separating distance (8 mm), thereby requiring the silicon steel flux path of a different size (6 mm×16 mm×0.5 mm). The schematics of setup 1 and setup 2 and their details and dimensions are provided in FIG. 1. Each magnetic setup was held in place by styrofoam and placed right underneath a well in a 24-well cell culture plate (Corning) as is illustrated in FIG. 2. The magnitudes and directions of the magnetic field ($\mu_0 H$) near the bottom of the well were simulated and mapped using the ANSYS software (electromagnetic package) as is shown in FIG. 3A (for Setup 1) and in FIG. 3B (for Setup 2). The results of the $\mu_0 H$ computations near the center of the well were verified by physical measurements using a Gauss meter.

Four replicates of setup 1 and of setup 2 were planned and built. The magnetic setups were placed apart from each other positioned under the 24-well cell culture plate with at least one empty well separation from all directions to minimize magnetic interferences. The configurations of the setup and cell placement are provided in FIG. 2. The scale bar at the center of FIG. 2 is 2 cm.

FIG. 2 shows the magnetic apparatus builds placed under the 24-well culture plates. As described above, each magnetic setup features two neodymium-iron-boron permanent magnet cylinders, arranged in alternating north-south magnetic polarization, connected by silicon steel bars. Setup 1 measures 18 mm from the magnets' centers, while Setup 2 measures 8 mm apart. One well from a 24-well plate sits on each setup as shown in FIG. 2, with dorsal root ganglia (DRG) being seeded at least in the center of the well in the 24-well plate, between the magnets. Placement is illustrated by the 3 dots in each cultured well of the 24-well plates shown in FIG. 2.

To determine the properties of the magnetic setups, a simulation was run in Ansys electronics v.17.2. (FIG. 3A and FIG. 3B). Setup 1, with its wider magnet placing, generated a small region of uniform in plane magnetic flux of ~150 Gauss as shown in FIG. 3A. In this region, the field vectors were parallel to the plates, pointing from north to south. DRG placed in the center of the plate would experience a low-strength field with in-plane field lines. Setup 2, with magnets only 8 mm apart, generated a center region with a flux gradient between about 400 and 500 Gauss. The field vectors point out of the plane above and below the plate, at a variety of angles as is shown in FIG. 3B. In FIG. 3A setup 1 features a weaker maximum center strength of 150 Gauss, but the field lines are more in-plane in the center, where DRG are seeded. In FIG. 3B, setup 2 features a higher maximum strength of 500 Gauss, but the gradient is non-uniform and the field lines are out of plane over the entire plate.

The DRG neurons were cultured in a modified Neurobasal-NGF media and grown in a cell culture incubator at 37° C. for four days, with experimental groups receiving one hour (per day) of low-strength static magnetic field stimulation. The overall area of neurite outgrowth after four days was characterized by fluorescent microscopy, and the influence of magnetic field was assessed by comparing overall neurite outgrowth area between stimulated and non-stimulated DRG.

Isolation of DRG is according to a previously published lab protocol (Puzan, M L, et al., 2018). DRG were isolated from Sprague-Dawley day 2 post-natal rat pups by removing from the entire spine and excess connective tissues were removed by hand using an 11-blade scalpel. Isolated and clean whole DRG were placed in Hibernate A media (BrainBits, Springfield, IL) in 50 mL centrifuge tubes, wrapped in parafilm. These wrapped centrifuge tubes were kept at 4° C. for up to one week.

Glass coverslips (12 mm, ThermoScientific) were sterilized via ultraviolet (UV) for 6 minutes on each side and placed in sterile 24-well plates (Corning). Sterilized coverslips were then plasma coated for 90 seconds with a Harrick Expanded Plasma Cleaner (PDC-002) to create a hydrophilic surface for the laminin coating to adhere to. The coverslips were then coated in a mixture containing laminin (Corning), 10× phosphate buffered saline (PBS) (SigmaAldrich), and sterile ultrapure MilliQ water, at a 1:1.5:5 ratio. The laminin-coated slips were then placed in a cell culture incubator at 37° C. for 1 hour, and then rinsed with sterile water prior to cell seeding.

Whole DRG were placed on the laminin-coated coverslips, placing three DRG on each slip, using sterile tweezers to manually arrange the DRG to ensure non-contacting distance and identical magnetic field exposure. The 3 dots in each cultured well of the 24-well plates shown in FIG. 2 illustrate placement. The DRG were then allowed to adhere to the laminin at room temperature for 10 minutes. A small drop of culture media (30 μL) [Neurobasal A media supplemented with 2 mM L-glutamine (Gibco), 0.5.% v/v *Penicillin/Streptomycin* (Sigma Aldrich), 50× B-27 (Gibco), and 25 ng/mL 2.5 S nerve growth factor (NGF, Gibco)] was placed on top of each DRG and the well plates were then incubated for 4 hours. 400 uL of media was then added to each well after adherence, and fresh medium changed after 24 hours. After 2 days, 500 uL of media was added to each well, ensuring not to disrupt the DRG. After 4 to 7 days, the cells were fixed and stained. The experiment was repeated in triplicate, creating three groups of data.

For immunostaining, all samples were fixed with 4% paraformaldehyde (PFA, Sigma Aldrich) for 20 minutes at room temperature and washed in triplicate with Hank's Buffered Saline Solution (HBSS, Sigma Aldrich). Samples were then permeabilized with a 0.1% Triton-X (Sigma Aldrich) in phosphate buffered saline (PBS) solution for 15 minutes at room temperature and again washed in triplicate. All samples were subsequently blocked in 2.5% goat serum (Sigma Aldrich) in PBS for 1 hour at room temperature or 4 C overnight. All DRG samples were stained with a 1:500 primary mouse anti-βIII tubulin antibody (Invitrogen) in goat serum for 1 hour at room temperature, followed by a triplicate rinse step. Secondary staining of 1:1000 AlexaFluor 488 phalloidin (Abcam), 1:1000 4',6-diamidino-2-phenylindol (DAPI, Invitrogen), and 1:500 goat anti-mouse AlexaFluor 647 (Abcam) in goat serum was done to visualize SC, cell nuclei, and actin filaments respectively. Immunostained samples were stored at 4 C for up to one week before imaging.

Immunostained samples were imaged on a Zeiss Axio Observer inverted fluorescent microscope (Carl Zeiss Microscopy LLC, Thornwood NY) with a 10× objective. Whole DRG photos were taken with 4×4 tiling and stitched with Zeiss Zen software to capture neurite extension, which was computed using a custom Matlab code to determine the total area in square pixels and square microns (Park, S, et al., 2015). Supplemental image analysis was performed using ImageJ (NIH Freeware).

Figure 7A:
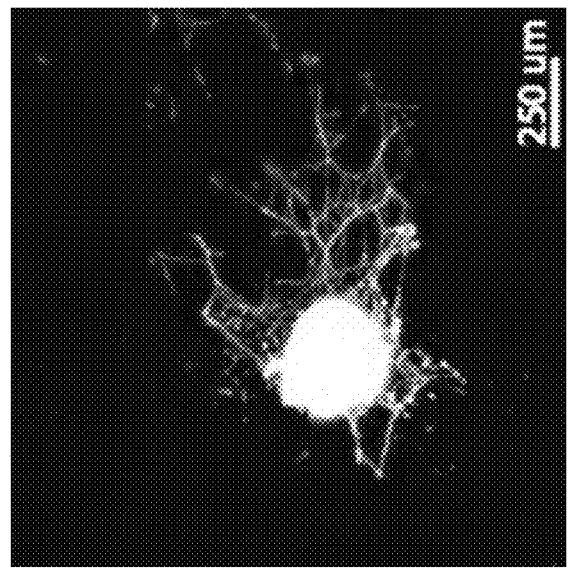
FIG. 7A shows a fluorescence microscope image of rodent DRG grown with no magnetic exposure, after 4 days.
Figure 7B:
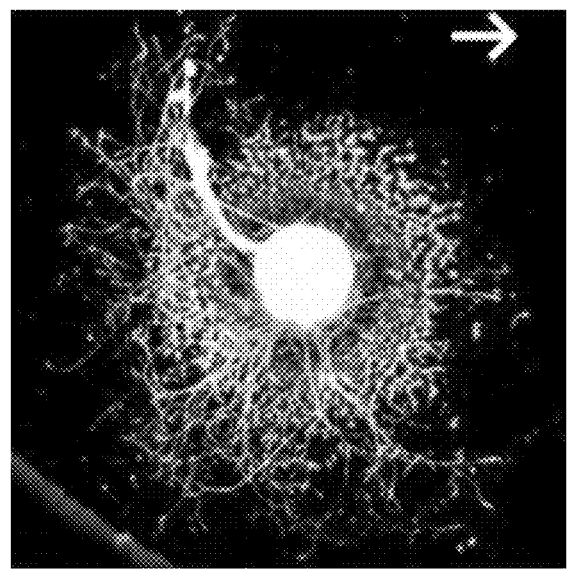
FIG. 7B shows a fluorescence microscope image of DRG grown (after 4 days) with 1 hour magnetic exposure per day for 3 days in the magnetic setup 1 (top of FIG. 1) for neurite growth. Staining is for beta-III tubulin. The field arrow indicates north magnetic field.
Figure 7C:
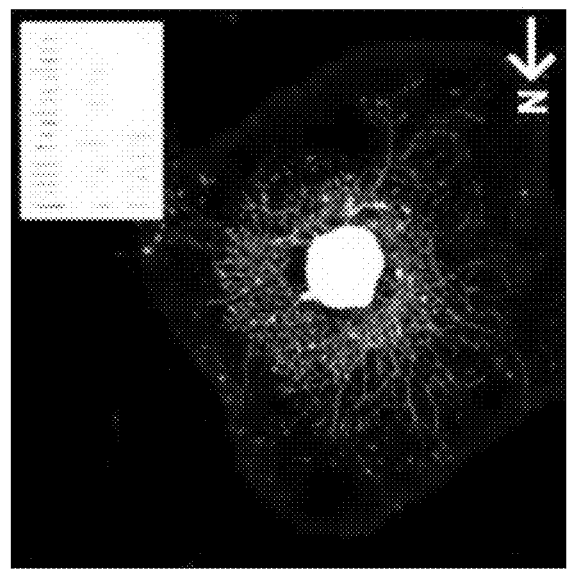
FIG. 7C shows a fluorescence microscope image of DRG grown (after 4 days) with 1 hour magnetic exposure per day for 3 days in the magnetic setup 2 (bottom of FIG. 1) for neurite growth. Staining is for beta-III tubulin. The field arrow indicates north magnetic field.

Experiments on the magnetic field exposure were performed in triplicate, with a minimum of six DRG. Each group of exposed DRG were considered with respect to their controls, which were grown outside of the magnetic apparatus but handled similarly. After 1 hour of magnetic field exposure per day for three days, DRG exposed to magnetic fields qualitatively grew outgrowths larger than the control, unstimulated samples (FIG. 7A, FIG. 7B, FIG. 7C). FIG. 7A shows DRG with no magnetic exposure after 4 days. FIG. 7B shows DRG from the first magnetic setup, and FIG. 7C shows DRG from the second magnetic setup. Field arrows indicate magnetic north. Each experimental group, consisting of DRG grown in both magnetic setups and a set of controls, saw an increase in outgrowth in magnetized DRG compared to their relative controls. Experimental group one with 29 control DRG grew an average outgrowth area of 12435 $\mu m^2 \pm 4966$ $\mu m^2$. Control DRG grown in experimental group two saw an average outgrowth area of 9064 $\mu m^2 \pm 4956$ $\mu m^2$ across 30 DRG, and experimental group three saw an average outgrowth area of 8389 $\mu m^2 \pm 3806$ $\mu m^2$ across 13 DRG.

Magnetic setup 1, whose field lines were more in plane with the neurites (FIG. 7B), saw an 87% increase (23328 $\mu m^2 \pm 5570$ $\mu m^2$) in outgrowth in the first experimental group with 7 DRG, 152% increase (22908 $\mu m^2 \pm 6921$ $\mu m^2$) in the second experimental group with 8 DRG, and 42% increase (11936 $\mu m^2 \pm 5225$ $\mu m^2$) in the third experimental group with 11 DRG. Magnetic setup 2, with more out-of-plane field lines (FIG. 7C), saw a 44% increase (17950 $\mu m^2 \pm 7980$ $\mu m^2$) in neuronal extension in the first group across 8 DRG, 116% increase (20229 $\mu m^2 \pm 3558$ $\mu m^2$) across 6 DRG, but only 6% more extension (8877 $\mu m^2 \pm \mu m^2$) in the third across 11 DRG.

Figure 8:
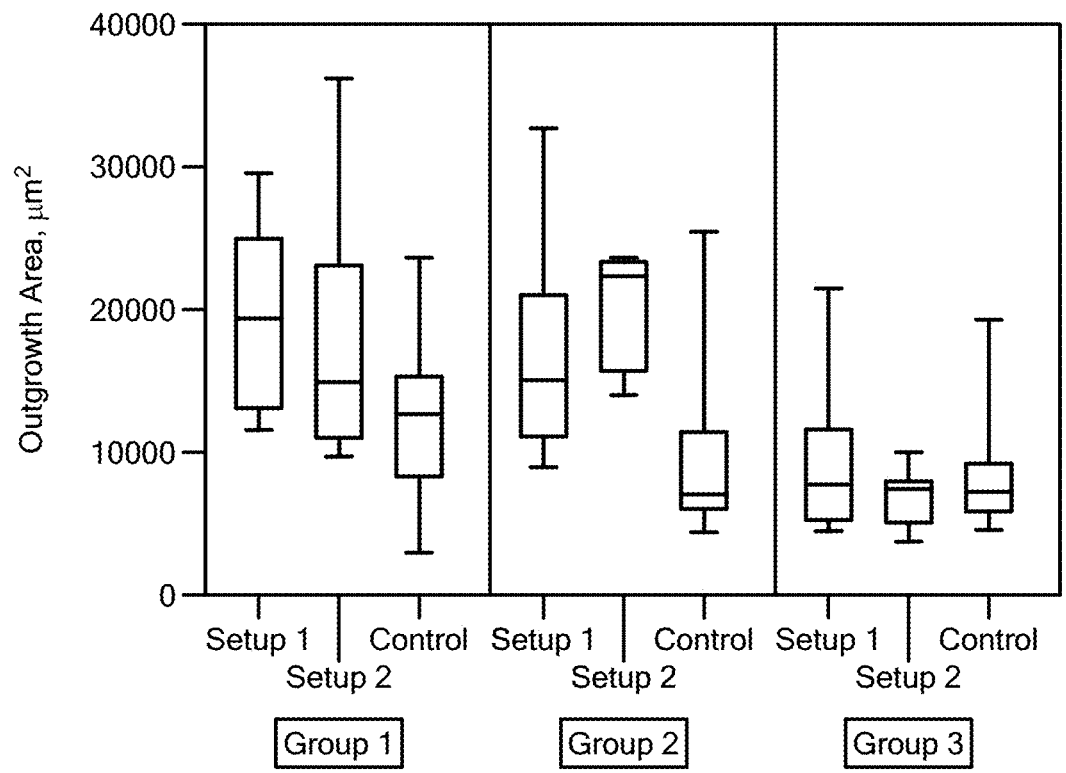
FIG. 8 shows box-and-whisker plots (outgrowth area in square microns v. growth condition) for DRG Group 1, Group 2, and Group 3, each grown in setup 1, setup 2, and control. A pooled comparison is shown in FIG. 9.

FIG. 8 shows box-and-whisker plot comparing outgrowth area for each setup in an experimental group compared to the relative control growth. Experimental group one saw 87% more growth in setup one and 44% more growth in setup two (Group 1, Plot 1). Experimental group two saw 152% more growth in setup one and 116% more growth in setup two (Group 2, Plot 2). Experimental group three saw 42% more growth in setup one and 5% more growth in setup two (Group 3, Plot 3).

Figure 9:
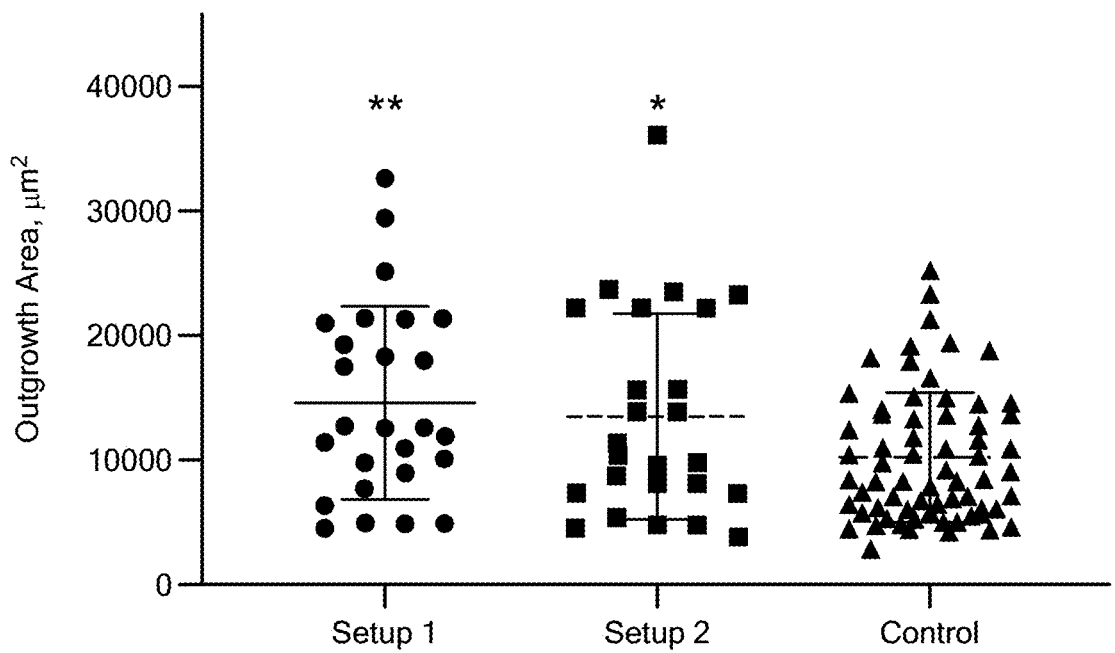
FIG. 9 shows a pooled comparison plot (outgrowth area in square microns v. growth condition), n=3, for setup 1, setup 2, and control.

DRG grew larger in the presence of magnetic fields. The difference between magnetic setups one and two is their magnetic field strength and the direction of the field lines (see FIG. 3A and FIG. 3B). The first magnetic setup has a midline strength of around 150 Gauss (15 mT), but the field lines are largely uniformly in plane. The second magnetic setup has a stronger field in the midline (between about 400 and 500 Gauss), but the field lines are not uniform in direction, leaving the plane in multiple directions. With data across all experimental groups pooled, overall outgrowth area for setup one was 42.5% larger on average compared to the pooled control values (p=0.0019). Overall outgrowth area was 31.7% larger in setup two compared to control values (p=0.0245). The statistical difference between the overall outgrowth area in setup one and setup two was not significant (p=0.6243) (FIG. 9). FIG. 9 shows comparison of pooled data (n=3) for both magnetic setups compared to overall control outgrowth. Setup one is very significantly larger (** indicates p<0.01), and setup two is significantly larger (* indicates p<0.05). Black end bars indicate standard deviation, and grey centered bars indicate mean.

DRG grew longer outgrowth in the first magnetic setup, despite the weaker field. This data points towards field lines having a major role in the length of neurite extensions based on the trends seen in FIG. 9 (also FIG. 8, FIG. 7A, FIG. 7B, and FIG. 7C). In all three experimental groups, average area of neurite extension was larger in the first magnetic setup over the second. However, a two tailed t-test did not indicate a significant difference between setup one and setup two. Data collected in this experiment demonstrates that a low-strength static magnetic field improves overall neurite outgrowth.

Figure 4B:
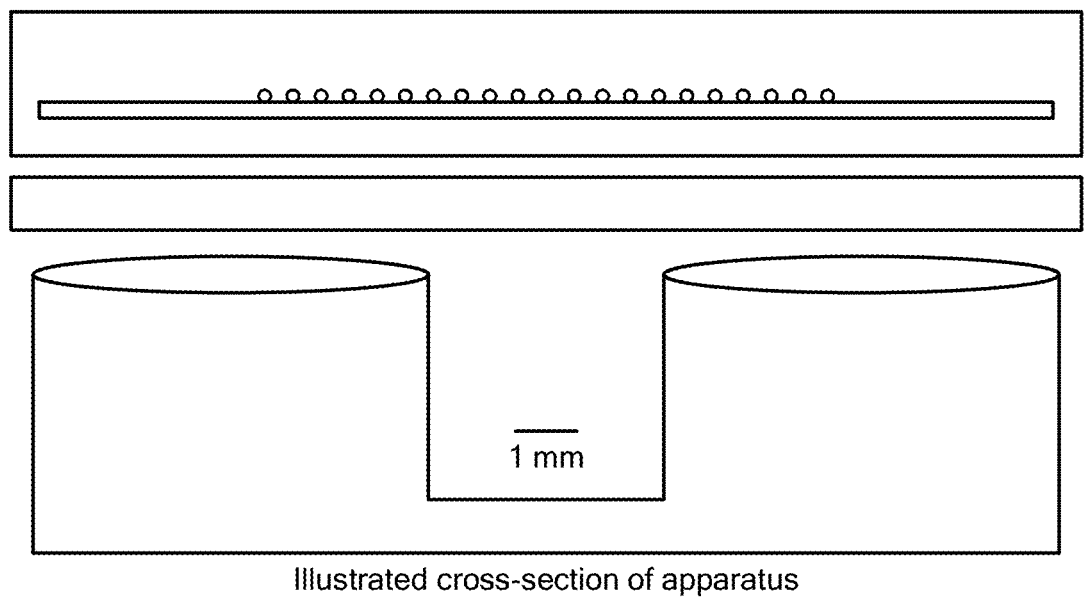
FIG. 4B shows a cross-section illustration of the magnetic setup shown in FIG. 4A, illustrating the placement of microwires at top. The scale bar at center is 1 mm.

To study the effects of magnetic field application on growing DRG, an apparatus was designed and built and is illustrated in FIG. 4A and FIG. 4B. FIG. 4A shows an illustration of the magnetic apparatus or setup including an Ansys software model of magnetic strength and field vectors. In FIG. 4A, the scale bar at left is from 1-2.5 tesla. In FIG. 4B, microwires are shown positioned (on glass cover slip) at top, and the scale bar at center is 1 mm. DRG growth was performed on a glass cover slip with the DRG without microwire mesh to distinguish between physical and magnetic cues. FIG. 5A shows an optical microscope image (20×) of rodent DRG neurons with new neurite growth, grown in the magnetic field. FIG. 5B shows an enlarged optical microscope image of FIG. 5A, enlarging the new neurite growth, which followed a linear path grown in the magnetic field. FIG. 6A shows an optical microscope image of DRG neurons with new neurite growth, grown without magnetic field. FIG. 6B shows an enlarged optical microscope image of FIG. 6A, enlarging the new neurite growth, which grew with no directionality when grown without a magnetic field.

Statistics and Data Analysis

Statistical calculations for magnetic setups, each with three experimental groups containing at least 6 experimental replicates, were done in GraphPad Prism 8 from DRG isolated from 30 animals on 3 different isolation days. Significance was determined using a one-way ANOVA and two tailed t-test with unequal variances, since there was only one set of variable data. Significance assumed at p<0.05 unless stated otherwise.

Example 4: Growth of Rodent Dorsal Root Ganglia with Amorphous Microwires

To determine if magnetically conductive microwires could provide synergistic topographical and magnetic growth cues for neurons, it was important to ensure the wires would provide aligned outgrowth patterns for the neurons. DRG were cultured and stained according to the procedure described above. Briefly, DRG were isolated from Sprague-Dawley day 2 post-natal rat pups and excess connective tissues were removed by hand using an 11-blade scalpel. Isolated and clean whole DRG were placed in Hibernate A media (BrainBits, Springfield, IL) at 4° C. for up to one week. An initial assessment demonstrated DRG growing (with imaging of stained neurites) on glass coated magnetic microwires followed the wires as is shown at the bottom of FIG. 15A, FIG. 15B, and FIG. 15C. Glass coated magnetic microwires ($Fe_{80}Si_{10}B_{10}$ core) are shown in parallel arrangement, perpendicular arrangement, and random arrangement in FIG. 15A (top), FIG. 15B (top), and FIG. 15C (top), respectively.

Sterilized coverslips were then plasma coated for 90 seconds with a Harrick Expanded Plasma Cleaner to create a hydrophilic surface for a laminin coating to adhere to. The coverslips were then coated in a mixture containing laminin, 10× phosphate buffered saline (PBS), and sterile ultrapure MilliQ water, at a 1:1.5:5 ratio. The laminin-coated slips were then placed in a cell culture incubator at 37° C. for 1 hour, and then rinsed with sterile water prior to cell seeding. Whole DRG were placed on the laminin-coated coverslips, placing three DRG on each slip, using sterile tweezers to manually arrange the DRG to ensure non-contacting distance and that all growth was on the wires. The DRG seeding regions are shown in FIG. 13. Seeding areas were far enough apart to prevent contact and were close enough to prevent growth off the wire mesh. The DRG were then allowed to adhere to the laminin at room temperature for 10 minutes. A small drop of culture media was placed on top of each DRG and the well plates were then incubated for 4 hours. 400 uL of media was then added to each well after adherence, and fresh medium changed after 24 hours. After 2 days, 500 uL of media was added to each well, ensuring not to disrupt the DRG. After 4 to 7 days, the cells were fixed and stained. The experiment was repeated in triplicate, creating three groups of data.

All samples were fixed with 4% paraformaldehyde for 20 minutes and washed in triplicate with Hank's Buffered Saline. Samples were then permeabilized with a 0.1% Triton-X in phosphate buffered saline (PBS) solution for 15 minutes and again washed in triplicate. All samples were subsequently blocked in 2.5% goat serum in PBS for 1 hour at room temperature or 4 C overnight. All DRG samples were stained with a 1:500 primary mouse anti-βIII tubulin antibody in goat serum for 1 hour at room temperature, followed by a triplicate rinse step. Secondary staining of 1:500 goat antimouse AlexaFluor 647 in goat serum was done to visualize actin filaments respectively. Immunostained samples were stored at 4° C. for up to one week before imaging.

Immunostained samples were imaged on a Zeiss Axio Observer inverted fluorescent microscope (Carl Zeiss Microscopy LLC, Thornwood NY) with a 10× objective. Whole DRG photos were taken with 4×4 tiling and stitched with Zeiss Zen software to capture neurite extension, which was computed using a custom Matlab code to determine the total area in square pixels and in square microns, and was amended to include a report on the longest calculated neurite in pixels. Supplemental image analysis was performed using ImageJ (NIH Freeware).

Experiments on the wire mesh were performed in triplicate, with a minimum of six DRG. Each group of DRG grown on wire mesh were considered with respect to their controls, which were grown on flat glass coverslips. The first and second experimental group were grown for four days, while the third experimental group grew for seven days. To determine if the overall results could be compared, a two tailed t-test was performed on the controls of the pooled four-day overall outgrowth area results and the seven-day results. The two data sets were not statistically different ($p=0.858$), and so the three were compared.

Comparison of control DRG outgrowth (FIG. 16A) and DRG grown on parallel-aligned wire mesh (FIG. 16B), stained for β-III tubulin (scale bar is 250 μm) show distinct differences in the neurite alignment. To measure the improvement in neurite outgrowth, the longest calculated neurite was compared between wire samples and control DRG. Longest achieved neurite was improved in all three experimental groups on wire mesh. The first experimental group saw a 17% increase (219.6 μm±64.3 μm) in longest measured neurite (FIG. 17A, left). The second experimental group saw a 39% increase (198.3 μm±29.6 μm) in longest neurite (FIG. 17A, center). The third experimental group saw a 38.7% increase (240.5 μm±87.8 μm) in longest neurite (FIG. 17A, right). With data across all experimental groups pooled (FIG. 17B), longest neurite seen in wire mesh samples was very significantly different than control ($p=0.020$). FIG. 17B shows pooled data (n=3) for wire meshes compared to control neurite length. Statistically, wire neurite length is significantly longer (** indicates $p<0.01$). End bars indicate standard deviation, and boxed bars indicate mean.

All experiments were repeated in triplicate (N=3) to ensure reliability of the results. Statistical significance was assessed using Student's t-test, with $p<0.05$ being statistically significant. Results are displayed as mean±standard deviation.

REFERENCES

Vazquez, Manuel; Editor: Magnetic Nano- and Microwires: Design, Synthesis, Properties and Applications (1st Edition); 21 May 2015 Print Book ISBN:978008100164.
Chiriac, Horia; Dumitru-Daniel Herea, and Sorin Corodeanu. "Microwire array for giant magneto-impedance detection of magnetic particles for biosensor prototype." Journal of Magnetism and Magnetic Materials 311.1 (2007): 425-428.
Hudak, Radovan, Rastislav Varga, Jozef Hudak, Dusan Praslicka, Irenej Polacek, Peter Klein, Rhimou El Kammouni, and Manuel Vazquez. "Influence of fixation on magnetic properties of glass-coated magnetic microwires for biomedical applications." IEEE Transactions on Magnetics 51, no. 1 (2015): 1-4.
Hernando, A., Vazquez, M., & Barandiaran, J. M. (1988). Metallic glasses and sensing applications. Journal of Physics E: Scientific Instruments, 21(12), 1129.
Hudak, R; Rastislav Varga, Irenej Polacek, Peter Klein, Ivan Skorvanek, Vladimir Komanicky, Rafael P. del. Real, and Manuel Vazquez. "Addition of molybdenum into amorphous glass-coated microwires usable as temperature sensors in biomedical applications." physica status solidi (a) 213, no. 2 (2016): 377-383.
S. A Baranov, "Cast Amorphous Magnetic Microwires for Medical Applications", Advances in Biotechnology and Microbiology, Vo. 8 (3) February 2018.
Hergt, R., Dutz, S., Müller, R., & Zeisberger, M. (2006). Magnetic particle hyperthermia: nanoparticle magnetism and materials development for cancer therapy. Journal of Physics: Condensed Matter, 18(38), S2919.
Zhukov, A.; J. Gonzalez, M. Vazquez, V. Larin, and A. Torcunov, Encyclopedia of Nanoscience and Nanotechnology, Vol. 6, ed. H. S. Nalwa, Valencia, C A: American Scientific Publishers, 2004, p. 365.
Vijayavenkataraman, S. (2020). Nerve guide conduits for peripheral nerve injury repair: A review on design, materials and fabrication methods. Acta Biomaterialia, 106, 54-69; doi.org/10.1016/j.actbio.2020.02.003.
University of Alabama at Birmingham, 2019, National Spinal Cord Injury Statistical Center, Facts and Figures at a Glance. Birmingham, AL:
nscisc.uab.edu/Public/
Facts%20and%20Figures%202020.pdf.
Ray, W. Z., & Mackinnon, S. E. (2010). Management of nerve gaps: Autografts, allografts, nerve transfers, and end-to-side neurorrhaphy. Experimental Neurology, 223 (1), 77-85.
https://doi.org/10.1016/j.expneurol.2009.03.031
Schmidt, C E, & Leach, J B (2003). Neural Tissue Engineering: Strategies for Repair and Regeneration. Annual Review of Biomedical Engineering, 5(1), 293-347.
Puzan, M. L., Legesse, B., Koppes, R. A., Fenniri, H., & Koppes, A. N. (2018). Bioactive Organic Rosette Nanotubes Support Sensory Neurite Outgrowth. ACS Biomaterials Science & Engineering; doi.org/10.1021/acsbiomaterials.8b00326.

Park, S., Koppes, R. A., Froriep, U. P., Jia, X., Achyuta, A. K. H., McLaughlin, B. L., & Anikeeva, P. (2015). Optogenetic control of nerve growth. Scientific Reports, 5(1). doi.org/10.1038/srep09669.

What is claimed is:

1. A system for nerve growth stimulation, the system comprising: (i) an implantable medical device comprising one or more magnetic microwires, and (ii) a device for producing an electric current, from outside a body of a subject, in the magnetic microwires of the implantable medical device when implanted in the body of the subject, wherein the microwires comprise a magnetic material comprising an amorphous phase of a metal, metal alloy, or a combination thereof, and wherein the magnetic material has a coercivity in the range from about 0.6 to about 2.5 Oe.

2. The system of claim 1, wherein the magnetic microwires comprise an alloy having a formula of $M_xMT_y$, wherein M is a metalloid, MT is a transition metal, x is an integer from 0 to 35, y is an integer from 1 to 85, and $(x+y) \leq 100$.

3. The system of claim 1, wherein the metal alloy is selected from the group consisting of CoFeSiB, CoMnSiB, CoFeSiBCrNi, and alloys containing Fe, B, and Si.

4. The system of claim 1, wherein one or more of said magnetic microwires comprises a sheath of non-metallic material covering the magnetic material, wherein the non-metallic material comprises a glass or polymer material.

5. The system of claim 4, wherein the glass comprises borosilicate, silica glass, an oxide, or a combination thereof.

6. The system of claim 4, wherein the polymer material is selected from the group consisting of laminin, collagen, poly(vinyl alcohol), poly-(D or L)-lactide, polyurethane acrylate, polycaprolactone, and poly(3,4-ethylenedioxythiophene) polystyrene sulfonate.

7. The system of claim 4, wherein the sheath comprises a releasable pharmaceutical agent or diagnostic agent.

8. The system of claim 7, wherein the pharmaceutical or diagnostic agent is selected from the group consisting of imaging agents, growth factors, cytokines, antibodies, aptamers, nucleic acids, and antitumor agents.

9. The system of claim 1, wherein the one or more microwires produce a magnetic field having a magnitude of about 100 Gauss to about 15000 Gauss.

10. The system of claim 1, comprising a plurality of magnetic microwires arranged in parallel or according to a geometric pattern.

11. A method for stimulating the growth of an injured nerve in a subject, the method comprising:
  (a) providing the system of claim 1;
  (b) implanting the one or more magnetic microwires in the subject at or near the injured nerve;
  (c) inducing or increasing a magnitude of a magnetic field or inducing an electric current in the one or more microwires using the stimulator device to apply a field from outside the subject's body;
  whereby growth of the injured nerve is stimulated.

12. The method of claim 11, wherein the microwires produce a magnetic field having a magnitude of about 100 Gauss to about 15000 Gauss.

13. The method of claim 11, wherein the injured nerve is severed and comprises a gap between severed ends, wherein the device comprises a plurality of magnetic microwires, and wherein the plurality of magnetic microwires form a parallel bundle that bridges the gap.

14. The method of claim 11, wherein the stimulated nerve growth is an increase in neurite number, density, directionality, length, or a combination thereof.

15. The method of claim 11, further comprising contacting the injured nerve with a growth enhancer.

16. A method of transferring energy or information in a subject, the method comprising:
  (a) implanting the one or more magnetic microwires of the system of claim 1 in the subject's body, the microwires traversing from a first location within the subject's body to a second location within the subject's body;
  (b) transferring energy or information to the one or more magnetic microwires at the first location; and
  (c) receiving energy or information from the one or more microwires at the second location.

17. The method of claim 16, wherein energy is transferred and received, and the received energy is used to release a pharmaceutical or diagnostic agent, to provide hyperthermic treatment of a tumor, to stimulate a nerve or growth of a nerve, to sense a biological condition, to actuate another medical device, to charge a battery of another medical device, or a combination thereof.

18. The method of claim 16, further comprising:
  (d) removing the magnetic microwires from the subject's body.

* * * * *